(12) United States Patent
Shen et al.

(10) Patent No.: US 11,103,551 B2
(45) Date of Patent: Aug. 31, 2021

(54) METHOD FOR TREATMENT OR PREVENTION OF A CANCER

(71) Applicants: Tang-Long Shen, Taipei (TW);
Yu-Ling Tai, Kaohsiung (TW);
Hsin-Jung Wu, Taipei (TW)

(72) Inventors: Tang-Long Shen, Taipei (TW);
Yu-Ling Tai, Kaohsiung (TW);
Hsin-Jung Wu, Taipei (TW)

(*) Notice: Subject to any disclaimer, the term of this patent is extended or adjusted under 35 U.S.C. 154(b) by 126 days.

(21) Appl. No.: 15/807,898

(22) Filed: Nov. 9, 2017

(65) Prior Publication Data

US 2018/0177845 A1 Jun. 28, 2018

Related U.S. Application Data

(60) Provisional application No. 62/419,949, filed on Nov. 9, 2016.

(51) Int. Cl.

| | |
|---|---|
| *A61P 35/00* | (2006.01) |
| *A61K 38/17* | (2006.01) |
| *A61K 38/45* | (2006.01) |
| *A61K 38/08* | (2019.01) |
| *A61K 38/06* | (2006.01) |
| *C07K 16/28* | (2006.01) |
| *C07K 16/44* | (2006.01) |
| *A61K 48/00* | (2006.01) |

(52) U.S. Cl.
CPC .......... *A61K 38/1777* (2013.01); *A61K 38/06* (2013.01); *A61K 38/08* (2013.01); *A61K 38/45* (2013.01); *A61P 35/00* (2018.01); *C07K 16/2839* (2013.01); *C07K 16/44* (2013.01); *C12Y 207/10002* (2013.01); *A61K 48/00* (2013.01); *C07K 2317/34* (2013.01); *C07K 2317/76* (2013.01); *C12N 2740/16043* (2013.01)

(58) Field of Classification Search
CPC .................................................. A61K 38/1777
USPC ....................................................... 424/139.1
See application file for complete search history.

(56) References Cited

FOREIGN PATENT DOCUMENTS

WO    WO 2016/061087 A1 *    4/2016

OTHER PUBLICATIONS

Takagi et al (J Biochem, 1980, 87: 1785-1793).*
Xu et al (Bioorganic & Medical Chemistry, 2013, 21: 388-394).*
Schaller et al (PNAS, 1992, 89: 5192-5196).*
Abdel-Ghany et al (JBC, 2002, 277(37):34391-34400).*

* cited by examiner

*Primary Examiner* — Sean E Aeder
(74) *Attorney, Agent, or Firm* — Juan Carlos A. Marquez; Marquez IP Law Office, PLLC

(57) ABSTRACT

The present invention is related to a method or a pharmaceutical composition for treatment or prevention of a cancer through blocking the interaction of β4 integrin and focal adhesion kinase (FAK).

3 Claims, 15 Drawing Sheets

Specification includes a Sequence Listing.

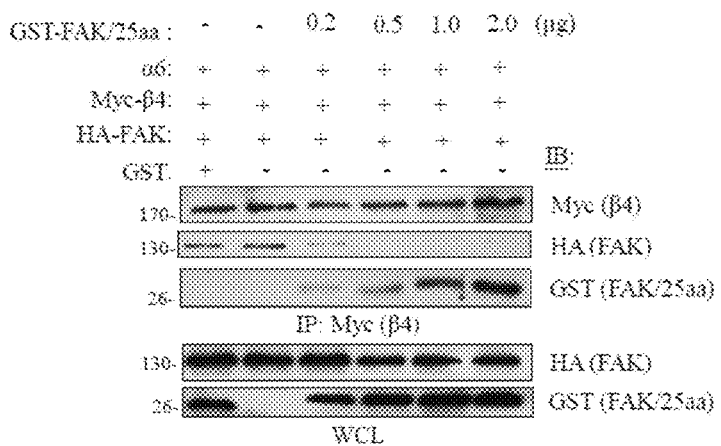
Fig. 4(a)
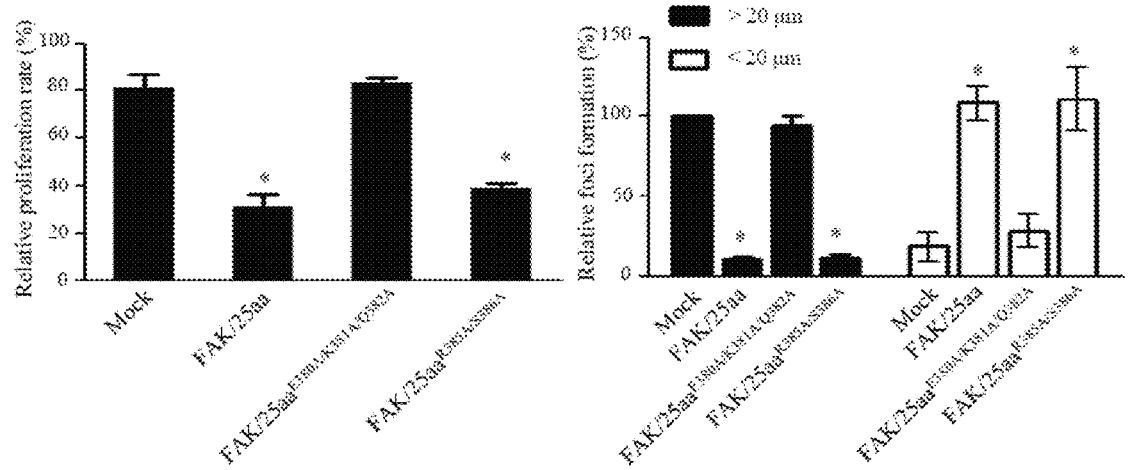
Fig. 4(b)
Fig. 4(c)
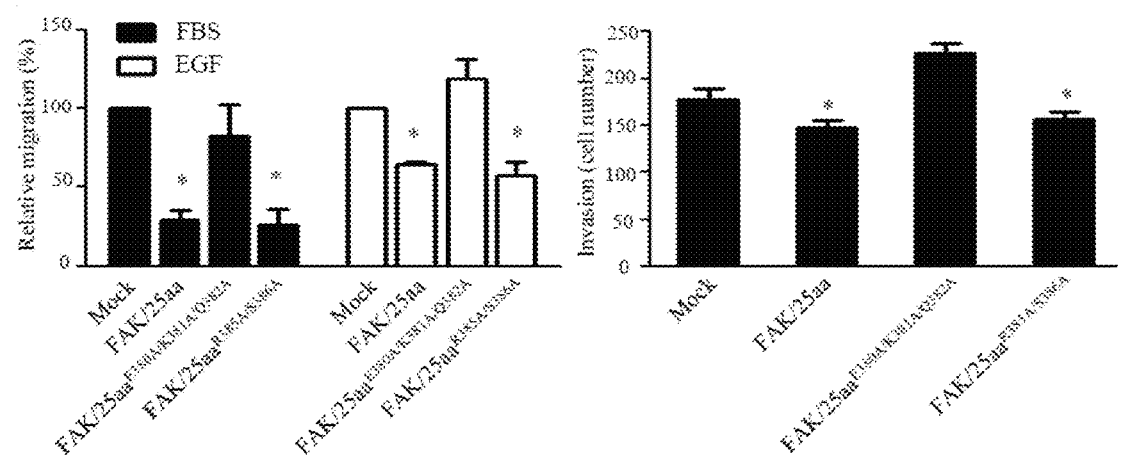
Fig. 4(d)
Fig. 4(e)

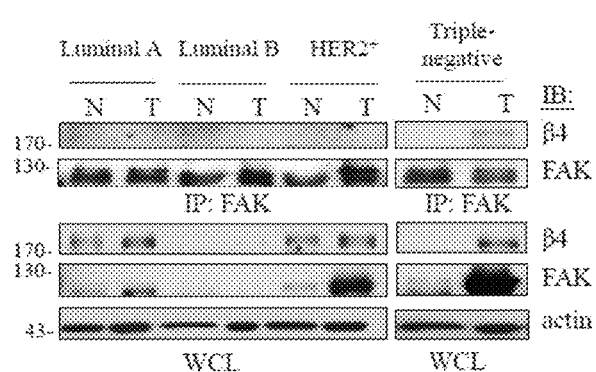
Fig. 6(a)
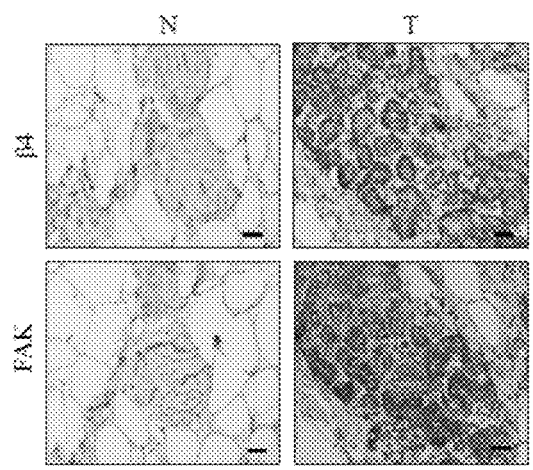
Fig. 6(b)
|  | β4 staining | | |
|---|---|---|---|
| FAK staining | Positive | Negative | Total |
| Positive | 27 (56 %) | 9 (19 %) | 36 |
| Negative | 4 (8 %) | 8 (17 %) | 12 |
| Total | 31 | 17 | 48 |
Fig. 6(c)
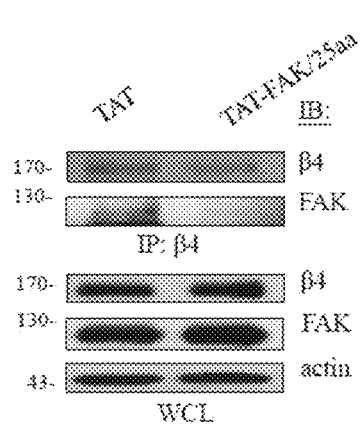 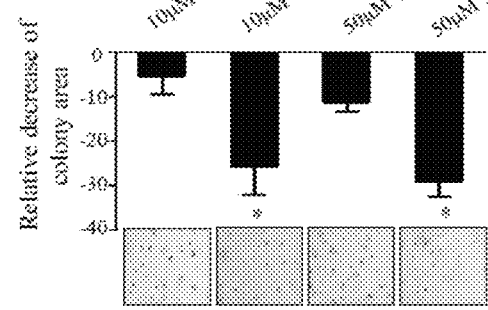
Fig. 6(d)

```
                         SEQUENCE LISTING

<160> NUMBER OF SEQ ID NOS: 11

<210> SEQ ID NO 1
<211> LENGTH: 3
<212> TYPE: PRT
<213> ORGANISM: Artificial Sequence
<220> FEATURE:
<223> OTHER INFORMATION: Synthetic

<400> SEQUENCE: 1

Phe Ala Lys
1

<210> SEQ ID NO 2
<211> LENGTH: 11
<212> TYPE: PRT
<213> ORGANISM: Artificial Sequence
<220> FEATURE:
<223> OTHER INFORMATION: Synthetic

<400> SEQUENCE: 2

Leu Ala Asn Asn Glu Lys Gln Gly Val Arg Ser
1               5                   10

<210> SEQ ID NO 3
<211> LENGTH: 25
<212> TYPE: PRT
<213> ORGANISM: Artificial Sequence
<220> FEATURE:
<223> OTHER INFORMATION: Synthetic

<400> SEQUENCE: 3

Leu Ala Asn Asn Glu Lys Gln Gly Val Arg Ser His Thr Val Ser Val
1               5                   10                  15

Ser Glu Thr Asp Asp Tyr Ala Glu Ile
            20                  25

<210> SEQ ID NO 4
<211> LENGTH: 400
<212> TYPE: PRT
<213> ORGANISM: Homo sapiens

<400> SEQUENCE: 4

Met Ala Ala Ala Tyr Leu Asp Pro Asn Leu Asn His Thr Pro Ser Ser
1               5                   10                  15

Ser Ala Lys Thr His Leu Gly Thr Gly Met Glu Arg Ser Pro Gly Ala
            20                  25                  30
```

Met Glu Arg Val Leu Lys Val Phe His Tyr Phe Glu Asn Ser Ser Glu
            35                  40                  45

Pro Thr Thr Trp Ala Ser Ile Ile Arg His Gly Asp Ala Thr Asp Val
 50                  55                  60

Arg Gly Ile Ile Gln Lys Ile Val Asp Cys His Lys Val Lys Asn Val
 65                  70                  75                  80

Ala Cys Tyr Gly Leu Arg Leu Ser His Leu Gln Ser Glu Glu Val His
                 85                  90                  95

Trp Leu His Leu Asp Met Gly Val Ser Asn Val Arg Glu Lys Phe Glu
                100                 105                 110

Leu Ala His Pro Pro Glu Glu Trp Lys Tyr Glu Leu Arg Ile Arg Tyr
            115                 120                 125

Leu Pro Lys Gly Phe Leu Asn Gln Phe Thr Glu Asp Lys Pro Thr Leu
130                 135                 140

Asn Phe Phe Tyr Gln Gln Val Lys Asn Asp Tyr Met Leu Glu Ile Ala
145                 150                 155                 160

Asp Gln Val Asp Gln Glu Ile Ala Leu Lys Leu Gly Cys Leu Glu Ile
                165                 170                 175

Arg Arg Ser Tyr Gly Glu Met Arg Gly Asn Ala Leu Glu Lys Lys Ser
            180                 185                 190

Asn Tyr Glu Val Leu Glu Lys Asp Val Gly Leu Arg Arg Phe Phe Pro
        195                 200                 205

Lys Ser Leu Leu Asp Ser Val Lys Ala Lys Thr Leu Arg Lys Leu Ile
210                 215                 220

Gln Gln Thr Phe Arg Gln Phe Ala Asn Leu Asn Arg Glu Glu Ser Ile
225                 230                 235                 240

Leu Lys Phe Phe Glu Ile Leu Ser Pro Val Tyr Arg Phe Asp Lys Glu
                245                 250                 255

Cys Phe Lys Cys Ala Leu Gly Ser Ser Trp Ile Ile Ser Val Glu Leu
            260                 265                 270

Ala Ile Gly Pro Glu Glu Gly Ile Ser Tyr Leu Thr Asp Lys Gly Ala
        275                 280                 285

Asn Pro Thr His Leu Ala Asp Phe Asn Gln Val Gln Thr Ile Gln Tyr
290                 295                 300

Ser Asn Ser Glu Asp Lys Asp Arg Lys Gly Met Leu Gln Leu Lys Ile
305                 310                 315                 320

Ala Gly Ala Pro Glu Pro Leu Thr Val Thr Ala Pro Ser Leu Thr Ile
                325                 330                 335

Ala Glu Asn Met Ala Asp Leu Ile Asp Gly Tyr Cys Arg Leu Val Asn
            340                 345                 350

Gly Ala Thr Gln Ser Phe Ile Ile Arg Pro Gln Lys Glu Gly Glu Arg
        355                 360                 365

Ala Leu Pro Ser Ile Pro Lys Leu Ala Asn Asn Glu Lys Gln Gly Val
370                 375                 380

Arg Ser His Thr Val Ser Val Ser Glu Thr Asp Asp Tyr Ala Glu Ile
385                 390                 395                 400

<210> SEQ ID NO 5
<211> LENGTH: 395
<212> TYPE: PRT
<213> ORGANISM: Homo sapiens

<400> SEQUENCE: 5

Asn Asn Met Gln Arg Pro Gly Phe Ala Thr His Ala Ala Ser Ile Asn
 1               5                  10                  15

Pro Thr Glu Leu Val Pro Tyr Gly Leu Ser Leu Arg Leu Ala Arg Leu
            20                  25                  30

Cys Thr Glu Asn Leu Leu Lys Pro Asp Thr Arg Glu Cys Ala Gln Leu
        35                  40                  45

Arg Gln Glu Val Glu Glu Asn Leu Asn Glu Val Tyr Arg Gln Ile Ser
    50                  55                  60

Gly Val His Lys Leu Gln Gln Thr Lys Phe Arg Gln Gln Pro Asn Ala
65                  70                  75                  80

Gly Lys Lys Gln Asp His Thr Ile Val Asp Thr Val Leu Met Ala Pro
                85                  90                  95

Arg Ser Ala Lys Pro Ala Leu Leu Lys Leu Thr Glu Lys Gln Val Glu
            100                 105                 110

Gln Arg Ala Phe His Asp Leu Lys Val Ala Pro Gly Tyr Tyr Thr Leu
        115                 120                 125

Thr Ala Asp Gln Asp Ala Arg Gly Met Val Glu Phe Gln Glu Gly Val
    130                 135                 140

Glu Leu Val Asp Val Arg Val Pro Leu Phe Ile Arg Pro Glu Asp Asp
145                 150                 155                 160

Asp Glu Lys Gln Leu Leu Val Glu Ala Ile Asp Val Pro Ala Gly Thr
                165                 170                 175

Ala Thr Leu Gly Arg Arg Leu Val Asn Ile Thr Ile Lys Glu Gln
            180                 185                 190

Ala Arg Asp Val Val Ser Phe Glu Gln Pro Glu Phe Ser Val Ser Arg
        195                 200                 205

Gly Asp Gln Val Ala Arg Ile Pro Val Ile Arg Val Leu Asp Gly
    210                 215                 220

Gly Lys Ser Gln Val Ser Tyr Arg Thr Gln Asp Gly Thr Ala Gln Gly
225                 230                 235                 240

Asn Arg Asp Tyr Ile Pro Val Glu Gly Glu Leu Leu Phe Gln Pro Gly
                245                 250                 255

Glu Ala Trp Lys Glu Leu Gln Val Lys Leu Leu Glu Leu Gln Glu Val
            260                 265                 270

Asp Ser Leu Leu Arg Gly Arg Gln Val Arg Arg Phe His Val Gln Leu
        275                 280                 285

Ser Asn Pro Lys Phe Gly Ala His Leu Gly Gln Pro His Ser Thr Thr
    290                 295                 300

Ile Ile Ile Arg Asp Pro Asp Glu Leu Asp Arg Ser Phe Thr Ser Gln
305                 310                 315                 320

Met Leu Ser Ser Gln Pro Pro His Gly Asp Leu Gly Ala Pro Gln
                325                 330                 335

Asn Pro Asn Ala Lys Ala Ala Gly Ser Arg Lys Ile His Phe Asn Trp
            340                 345                 350

Leu Pro Pro Ser Gly Lys Pro Met Gly Tyr Arg Val Lys Tyr Trp Ile
        355                 360                 365

Gln Gly Asp Ser Glu Ser Glu Ala His Leu Leu Asp Ser Lys Val Pro
    370                 375                 380

Ser Val Glu Leu Thr Asn Leu Tyr Pro Tyr Cys
385                 390                 395

<210> SEQ ID NO 6
<211> LENGTH: 9
<212> TYPE: DNA
<213> ORGANISM: Artificial Sequence
<220> FEATURE:

```
<223> OTHER INFORMATION: Synthetic

<400> SEQUENCE: 6 gagaagcaa                                                                9

<210> SEQ ID NO 7
<211> LENGTH: 33
<212> TYPE: DNA
<213> ORGANISM: Artificial Sequence
<220> FEATURE:
<223> OTHER INFORMATION: Synthetic

<400> SEQUENCE: 7
ctggccaaca atgagaagca aggagtaagg tcg                                     33

<210> SEQ ID NO 8
<211> LENGTH: 20
<212> TYPE: DNA
<213> ORGANISM: Artificial Sequence
<220> FEATURE:
<223> OTHER INFORMATION: Synthetic

<400> SEQUENCE: 8
ccttccccgc agttaccttt                                                    20

<210> SEQ ID NO 9
<211> LENGTH: 12
<212> TYPE: PRT
<213> ORGANISM: Artificial Sequence
<220> FEATURE:
<223> OTHER INFORMATION: Synthetic

<400> SEQUENCE: 9

Gly Arg Lys Lys Arg Arg Gln Arg Arg Arg Pro Gln
1               5                   10

<210> SEQ ID NO 10
<211> LENGTH: 21
<212> TYPE: DNA
<213> ORGANISM: Artificial Sequence
<220> FEATURE:
<223> OTHER INFORMATION: Synthetic

<400> SEQUENCE: 10
cccatgaaga aagtgctggt t                                                  21

<210> SEQ ID NO 11
<211> LENGTH: 21
<212> TYPE: DNA
<213> ORGANISM: Artificial Sequence
<220> FEATURE:
<223> OTHER INFORMATION: Synthetic

<400> SEQUENCE: 11
gagggtgtca tcaccattga a                                                  21
```

METHOD FOR TREATMENT OR PREVENTION OF A CANCER

CROSS REFERENCE TO RELATED APPLICATIONS

This application claims priority to U.S. Provisional Application No. 62/419,949 filed on Nov. 9, 2016, entitled "METHOD FOR TREATMENT OR PREVENTION OF A CANCER."

FIELD OF THE INVENTION

The present invention provides a method for treating or preventing a cancer.

BACKGROUND OF THE INVENTION

Focal adhesion kinase (FAK) is a non-receptor tyrosine kinase serving as a mediator involved in transmitting integrin- and growth factor receptor-regulated signals [5]. In accordance with its role in regulating cellular functions [6], overexpression and activation of FAK is believed to trigger tumor progression and metastasis [6-8]. In particular, overexpression of FAK has been associated with liver metastases of colon cancer, which suggests that FAK promotes tumor malignancy [9]. Alternatively, FAK autophosphorylation at tyrosine 397 has been proposed to contribute to the malignant progression of human colon cancer [10-12]. Indeed, FAK phosphorylation at tyrosine 397 is a key point for FAK-mediated signaling that governs tumor malignancy [13-17]. Nevertheless, the molecular mechanism by which upstream receptors, including integrins and growth factor receptors, coordinately activate FAK Tyr397 autophosphorylation and subsequently result in downstream signaling in triggering the development of tumor malignancies remains unclear. A clear illustration of the mechanistic details of FAK activation will facilitate the development of therapeutic agents for malignant tumors.

In addition to its participation in the assembly of hemidesmosomes in epithelial cells [18], β4 integrin is involved in the progression of several cancers, such as breast, colorectal, and lung cancers [19-21]. For example, a significant up-regulation of β4 integrin expression was positively correlated with colon cancer progression [20]. Due to a lack of any intrinsic kinase activity, β4 integrin is speculated to employ adaptor proteins and/or non-receptor tyrosine kinases to regulate tumor malignancy [22, 23]. For instance, the cytoplasmic signaling domain of β4 integrin known to activate the PI-3K or MAPK cascades is necessary to modulate tumor malignancies [22, 24-26].

Although the overexpression of either β4 integrin or FAK has been reported to correlate with the progression of colon cancer malignancies [20, 27, 28], the relationship between the two molecules involved in cancer progression remains unclear.

It is still desirable to find a new approach to develop a therapy or therapeutic agent for treating a cancer.

BRIEF SUMMARY OF THE INVENTION

It is unexpectedly found in the present invention that are effective in treatment or prevention of a cancer through blocking of the interaction of β4 integrin and FAK.

Accordingly, in one aspect, the present invention provides a method for treatment or prevention of a cancer, comprising administering to a subject in need thereof an agent or a molecule effective to block the binding of β4 integrin and focal adhesion kinase (FAK).

In another aspect, the present invention provides a pharmaceutical composition for treatment or prevention of a cancer comprising an agent effective to block the binding of β4 integrin and focal adhesion kinase (FAK) and a pharmaceutically acceptable carrier.

In further aspect, the present invention provides a use of an agent or a molecule effective to block the binding of β4 integrin and, focal adhesion kinase (FAK) for manufacturing a medicament for treating or preventing a cancer.

In one embodiment of the present invention, the cancer is a cancer in association of regulation of epidermal growth factor (EGF) receptor. Examples of the cancer include but are not limited to breast cancer, colon cancer, skin cancer, lung cancer and stomach cancer.

In a further aspect, the invention provide an, agent for treatment or prevention of a cancer, which is selected from the group consisting of
(1) a peptide derived from FAK, containing at least $Glu^{380}$-$Lys^{381}$-$Gln^{382}$ (FAK/3aa, SEQ ID NO: 1), or a mimetic peptide thereof;
(2) a peptide derived from β4 integrin;
(3) an agent for gene therapy, which is a polynucleotide coding for an amino acid fragment of FAK containing at least FAK/3aa SEQ ID NO: 1);
(4) an antibody which is generated against a peptide derived from FAK, containing at least FAK/3aa (SEQ ID NO: 1); or an antibody which is generated against a peptide derived from β4 integrin; and
(5) a compound which blocks the binding of β4 integrin and focal adhesion kinase (FAK).

Those and other aspects of the present invention may be further clarified by the following descriptions and drawings of preferred embodiments. Although there may be changes or modifications therein, they would not betray the spirit and scope of the novel ideas disclosed in the present invention.

BRIEF DESCRIPTION OF THE DRAWINGS

The drawings presenting the preferred embodiments of the present invention are aimed at explaining the present invention. It should be understood that the present invention is not limited to the preferred embodiments shown.

FIG. 1(a) shows that varied human cancer cell lines were analyzed by Western blot analysis with anti-β4 integrin, anti-FAK, or anti-phospho-Tyr397 antibody, showing an interaction between β4 integrin and FAK. The human mammary epithelial cell line MCF10A was used as a normal control. In FIG. 1(k) and FIG. 1(l), co-immunoprecipitated β4 integrin or FAK fragments were visualized by anti-Myc or anti-HA antibodies, respectively. FIG. 1(n) shows a summary of various β4 integrin truncated mutants capable of interaction with FAK is listed. β4 integrin truncated mutants, including cytodornain (containing the region between transmembrane domain, TM, and FNIII repeat 1). FNIII(1-2) (containing FNIII repeats 1 and 2), FNIII(1-2-L) (containing FNIII repeats 1 and 2 and linker segment), FNIII(3-4-C) (containing FNIII repeats 3, 4 and carboxyl end), and those lack either the whole cytoplasmic domain (designated as Δcyto), the FNIII repeats 3 and 4 (designated as ΔFNIII 3-4), or the linker region to the carboxyl end (designated as ΔFNIII L-3-4).

FIG. 2(a) shows that varied human cancer cell lines were subjected to Western blot analysis to analyze the phosphorylation and expression of indicated signal molecules. FIG. 2(b) shows that MDA-MB-231 cells were transfected with HA-tagged wild-type Src, constitutively active Src$^{Y527F}$, and kinase-dead Src$^{K295M}$ to examine the effect of Src kinase activity on the interaction between β4 integrin and FAK. The results indicated that Src kinase activity promotes the interaction between β4 integrin and FAK. FIG. 2(c) shows that MDA-MB-231 cells were treated with DMSO, PP2 (10 μM), or PP3 (10 μM) to examine the effect of Src kinase activity on the tyrosine phosphorylation of β4 integrin and FAK as well as the interaction between α4 integrin and FAK. FIG. 2(d) shows that phospho-tyrosine point mutation mutants of α4 integrin, as indicated, were analyzed to examine their competence for interacting with FAK. The mean of relative interaction between α4 integrin and FAK (normalized to wild-type α4 integrin shown as 1.0) was measured. FIG. 2(e) shows that serum-starved MDA-MB-231 cells were stimulated with EGF (10 ng/ml) in the presence of PP2 (10 μM) or PP3 (10 μM) to examine the effect of EGF/Src signaling on the tyrosine phosphorylation of β4 integrin and FAK as well as the interaction between β4 integrin and FAX. FIG. 2(f) shows that serum-starved MCF7 cells were treated with EGF (10 ng/ml) to examine the co-localization of β4 integrin (red) and FAX (green) by immunofluorescent staining. Arrows indicate the distribution of FAX at focal adhesions and/or on the peripheral plasma membrane. Arrowheads indicate the localization of β4 integrin on the plasma membrane (Scale bars, 20 μm). Each experiment was repeated at least three independent times. All cropped blots were run under the same experimental conditions.

FIG. 3(a) shows that Cell lysates from shLuc- or shβ4 integrin-infected MDA-MB-231 cells were subjected to Western blot analysis with anti-β4 integrin, anti-FAK, and anti-phospho-Tyr397 antibodies to examine the effect on the tyrosine phosphorylation of FAK. FIG. 3(b) shows that the phospho-Tyr$^{397}$ level was decreased in proportion with the increase of β4 integrin/tailless expression. FIG. 3(c) shows FAK/25aa (the 376$^{th}$ to the 400$^{th}$ amino acids), or its triple (FAK/25aa$^{E380A/K381A/Q382A}$) or double (FAK/25aa$^{R385A/S386A}$) mutant effects on full-length FAK phosphorylation are shown, FIG. 3(d) shows that FAK kinase activity and phospho-Tyr$^{397}$ were not a prerequisite for interacting with β4 integrin. The ΔN, which lacks the β4 integrin binding motif, was used as a negative control. FIG. 3(e) shows that MDA-MB-231 cells were transfected with GFP-tagged FAK/25aa, or its triple (FAK/25aa$^{E380A/K381A/Q382A}$) or double (FAK/25aa$^{R385A/S386A}$) mutant to reveal potential downstream signaling, including pTyr705-STAT3, pThr180/Tyr182-p38MAFK, pThr183/Tyr 185-JNKMAPK, pThr202/Tyr204-ERKMAPK, pSer473-AKT, and pTyr118-paxillin. Each experiment was repeated at least three independent times. All cropped blots were run under the same experimental conditions.

FIGS. 4(a)-4(e) show the β4 integrin/FAK complex regulates tumor malignancy in vitro. FIG. 4(a) shows that the FAK/25aa peptide competes with full-length FAK for binding to β4 integrin. The experiment was repeated at least three independent times. FIG. 4(b) shows the results of the cropped blots (which were run under the same experimental conditions), in which MDA-MB-231 cells over-expressing GFP-tagged FAK/25aa or its triple (FAK/25aa$^{E380A/K381A/Q382A}$) or double (FAK/25aa$^{R385A/S386A}$) mutant were subjected to cell proliferation assays using BrdU incorporation analysis. FIG. 4(c) shows the results of the soft agar assay in the presence of EGF (10 ng/ml) to examine the capability for anchorage-independent growth. FIG. 4(d) shows the results of the cell migration assay in a modified Boyden chamber. FIG. 4(e) shows the results of the Matrigel invasion assay to examine the capability for invasiveness in these tumor cells. All result shown as the mean±s.d. from three independent experiments (*, p<0.05, value was in comparison to the corresponding mock control).

FIG. 5(a) shows that MDA-MB-231 cells stably over-expressing GFP-tagged FAK/25aa or its triple (FAK/25aa$^{E380A/K381A/Q382A}$) or double (FAK/25aa$^{R385A/S386A}$) mutant were injected into the 3$^{rd}$ mammary fat pad of nude mice to examine tumor mass and protein expression of the xenograft tumors in vivo. Scale bar, 1 cm. The results are shown as the mean±s.d. n=3 for mock, n=5 for others (*, p<005, value was in comparison to mock. The cropped blots were run under the same experimental conditions). FIG. 5(b) shows that the above MDA-MB-231 stable cells were injected into the tail veins of nude mice to measure tumor metastasis in vivo. The kinetics of breast cancer metastasis to the lung were measured by bioluminescence and representative images are shown at day 0, 63, and 84 after injection. The graph shows the relative photon flux at day 84 after injection. The results are shown as the mean±s.d. n=3 for mock, n=5 for others (*, p<0.05, value was in comparison to moc)k. FIG. 5(c) shows the lung metastatic nodules (left column), H&E staining (the second and third columns) and immunohistochemical analysis of GFP protein expression (the fourth column) at lung metastatic sites at day 84 after injection1 wherein lung metastatic nodules were indicated by arrowheads and "M" (Scale bars, 1 cm (left column), 200 µm (the second from left), 100 µm (the third and fourth columns)).

FIGS. 6(a)-6(d) show a positive correlation between β4 integrin and FAK expression in patients with triple-negative breast cancer can be therapeutically targeted. FIG. 6(a) shows that homogenized normal (N) and tumor (T) tissue lysates of four patients with luminal A, luminal B, HER2$^+$, or triple-negative breast cancer were collected and subjected to immunoprecipitation. FAK co-immunoprecipitated β4 integrin was visualized by Western blot analysis. FIG. 6(b) shows the immunohistochemical staining for β4 integrin and FAK in human triple-negative breast cancer (T) and adjacent non-cancerous breast (N) tissues (Scale bars, 20 µm). FIG. 6(c) shows the results of the Spearman's γ correlation test, indicating that up-regulation of both β4 integrin and FAK was significantly correlated in 48 human triple-negative breast cancers (γ=0.3772; p=0.0082. All cropped blots were run under the same experimental conditions). FIG. 6(d) shows that a synthetic peptide targeting to the β4 integrin/FAK complex formation was druggable against triple-negative breast cancer tumorigenicity. MDA-MB-231 cells were treated with TAT (10 µM) or TAT-tagged FAK/25aa (10 µM) peptides to examine the effect on the interaction between β4 integrin and FAK by co-immunoprecipitation and Western blot analyses (Left panel). MDA-MB-231 cells were subjected to soft agar assay in the presence of the TAT-tagged FAX/25aa peptide (10 µM or 50 µM) to examine the capability for anchorage-independent growth of tumor cells (Right panel). The relative decrease of colony area (normalized to non-treated cells defined as 0) was shown (right and top). The result showed the mean±s.d. from three independent experiments (*, p<0.05, value was in comparison to the untreated control). Representative images of cells treated with TAT or TAT-tagged FAK/25aa peptides were photographed and shown (right and bottom).

FIG. 8(A) shows the results of the representative immunohistochemical staining for β4 integrin in stage I and III colon cancer tissues (top) (Scale bars, 20 µm). Analysis of β4 integrin expression profiles in early (stage I) and advanced (stage II+III-+IV; stage II, stage III, and stage IV) stage tumors by Fisher's exact test (bottom) (p=0.0157). FIG. 8(B) shows the results of the representative immunohistochernical staining for FAK in stage I and III colon cancer tissues (top) (Scale bars, 20 µm). Analysis of FAK expression profiles in early (stage I) and advanced (stage II+III+IV; stage II, stage III, and stage IV) stage tumors by Fisher's exact test (bottom) (p=0.0091). FIG. 8(C) shows the positive correlation between β4 integrin and FAK expression in 67 human colon cancer tissues; and the results were analyzed with a Spearman's γ correlation test (γ=0.2860; p=0.0189).

FIG. 9(A) shows that homogenized normal and tumor tissue lysates of patients with colon cancer were collected and subjected to immunoprecipitation. FAK was co-immunoprecipitated with β4 integrin, and the autophosphorylation level of FAK at Tyr397 was visualized by Western blotting. FIG. 9(B) shows that HCT-116, HeLa, and HEK-293 cell lines were analyzed by Western blotting with anti-β4 integrin, anti-FAK, and anti-phospho-Tyr397 antibodies. Cell lysates from HCT-116, HeLa, and HEK-293 cell lines were collected and subjected to immunoprecipitation. The interaction between β4 integrin and FAK were visualized by Western blotting. FIG. 9(C) shows that the cell lysates from HCT-116 cells were incubated with the GST-FAK(N375 or GST-FAK/N400 recombinant proteins. Then, GST-tagged fusion proteins were pulled down with GST-conjugated beads, followed by Western blotting with an anti-β4 integrin antibody. FIG. 9(D) shows that by immunoprecipitation and Western blotting, the triple mutant (FAK$^{E350/K381/Q382}$) ablated the interaction with β4 integrin compared with wild-type FAK or the double mutant (FAK$^{R385/S386}$) in HCT-116 cells. FIG. 9(E) shows that the FAK/25aa motif but not the FAK/25aa$^{E380/K381A/Q382A}$ motif ablated the interaction between β4 integrin and FAK in HCT-116 cells. FIG. 9(F) shows that HEK-293 cells were transfected with HA-tagged β4 integrin cytodomain (β4-cyto) or its truncated mutants, i.e., Na$^+$/Ca$^{2+}$ exchanger homologous motif (β4-CalX) and CalX truncation (deletion of CalX region, β4-deCalX), to investigate FAK binding sites on β4 integrin.

FIG. 10(A) shows that cell lysates from slaLuc- or shβ4 integrin-infected HCT-116 cells were collected and subjected to Western blotting with anti-β4 integrin, anti-FAK, and anti-phospho-Tyr397 antibodies to examine the effect of β4 integrin on phospho-Tyr397 of FAK. FIG. 10(B) shows that HCT-116 cells were treated with DMSO or PF573-228 (10 µM) to investigate the effect of FAK autophosphorylation at Tyr397 and the formation of β4 integrin/FAK complexes.

The results indicated that phospho-Tyr397 was not required for FAK to interact with β4 integrin. FIG. 10(C) shows that HCT-116 cells were transfected with GFP-FAK/25aa (amino acids 376 to 400) or its triple (FAK/25aa$^{E380A/K381A/Q382A}$) or double (FAK/25aa$^{R385A/S386A}$) mutant to investigate the effect of β4 integrin/FAK complexes on FAK autophosphorylation at Tyr397.

FIG. 11A shows that since Src activity is essential for the β4 integrin/FAK complex formation as well as FAK activation in human colon cancer, the β4 integrin/FAK complex formation was increased in HCT-116 cells transfected with a constitutively active Sre expression construct (Y527F). FIG. 11B shows that the pharmacological blockade of Src activity by PP2 decreased the β4 integrin/FAK complex formation and to alleviate the FAK, activation. FIG. 11C shows that since EGF/EGFR signaling is essential for β4 integrin-mediated cancer functions through SFKs activity, both the β4 integrin and FAK association and FAK activation can be elevated in response to EGF stimulation but is ablated in the presence of PP2.

FIG. 13A shows cells over-expressing GFP-FAK/25aa were subjected to a cell proliferation assay using BrdU incorporation analysis. Here. FAK and FRNK transfectants were used as controls. FIG. 13B shows that cells over-expressing GFP-FAK/25aa or its triple (FAK/25aa$^{E380A/K381A/Q382A}$) or double (FAK/25aa$^{R385A/S386A}$) mutant were subjected to a soft agar assay to examine their anchorage-independent growth. All results are presented as the means±s.d. from at least three independent experiments (*, p<0.05, compared with the corresponding mock control). FIG. 13C shows that HCT-116 cells stably transfected with GFP-tagged FAK/25aa or its triple (FAK/25aa$^{E380A/K381A/Q382A}$) or double (FAK/25aa$^{R385A/S386}$A) mutant, as well as a mock transfected control, that had been selected using 500 µg/ml G418 for 2 weeks. An in vivo tumorigenicity assay was conducted using a xenograft mouse model by subcutaneously injecting cells described above into SCID mice. Mice were sacrificed 21 days after tumor injection. Tumor mass (left, top), protein expression (left, bottom), and tumor weight (right) of the xenografts were measured. Five mice were assessed for each group (Scale bar, 1 cm. *, p<0.05, compared with the corresponding mock control).

FIG. 14(A) shows that cell lysates from HCT-116 cells treated with or without FAK inhibitor PF-573,228 were subjected to Western blotting with anti-FAK, anti-phospho-Tyr397, anti-AKT, and phospho-Ser473 antibodies. FIG. 14(B) shows that HCT-116 cells treated with or without FAK inhibitor PF-573,228 were subjected to a soft agar assay to examine anchorage-independent growth. DMSO was used as control. The results are presented as the means±s.d. from three independent experiments (*, p<0.05, compared with the DMSO control).

DETAILED DESCRIPTION OF THE INVENTION

Figure 1A:
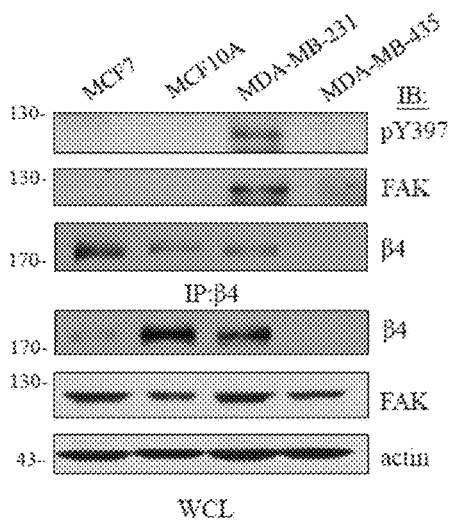
FIGS. 1(a)-1(n) show the physical interaction of β4 integrin and FAK is associated with tumor malignancy in vivo and in vitro.

Unless defined otherwise, all technical and scientific terms used herein have the same meanings as commonly understood by one of skill in the art to which this invention belongs.

Unless clearly specified herein, meanings of the articles "a," "an," and "said" all include the plural form of "more than one." Therefore, for example, when the term "a component" is used, it includes multiple said components and equivalents known to those of common knowledge in said field.

As used herein, the term "subject" refers to a human or a mammal, such as a patient, a companion animal (e.g., dog, cat, and the like), a farm animal (e.g., cow, sheep, pig, horse, and the like) or a laboratory animal (e.g., rat, mouse, rabbit, and the like).

The term "carrier" or "pharmaceutically acceptable carrier" used herein includes, but not limited to, pharmaceutically acceptable excipients, fillers, diluents, or the like, including those well known to one of ordinary skills in the pharmaceutical field.

In the invention, it was investigated that the EGFR/Src signaling-regulated β4 integrin/FAK complex is involved in cancer malignancy. In light of β4 integrin-mediated FAK activation and signaling involved in tumor progression, the clinicopathological correlation between β4 integrin and FAK signaling and human cancer were clarified. Subsequently, the mechanistic details of FAK activation via β4 integrity leading to malignant progression of a cancer were explored.

The present invention provides a method for treatment or prevention of a cancer, comprising administering to a subject in need thereof an agent at the amount effective to block the interaction of β4 integrin and Focal adhesion kinase (FAK).

On the other hand, the present invention provides a use of an, agent or a molecule effective to block the binding of β4 integrin and focal adhesion kinase (FAX) for manufacturing a medicament for treating or preventing a cancer.

The present invention also provides a pharmaceutical composition comprising an agent at the amount effective to block the interaction of β4 integrin and focal adhesion kinase (FAK) and a pharmaceutically acceptable carrier.

According to the invention, the cancer is a cancer in association of regulation of epidermal growth factor (EGF) receptor. Examples of the cancer include but are not limited to breast cancer, colon cancer, skin cancer, lung cancer and stomach cancer.

In the present invention, it is unexpectedly found that the 380th, 381th and 382th residues (i.e., the Glu$^{380}$, Lys$^{381}$ and Gln$^{382}$ amino acids) out from the amino acids of FAK is critically involved in the interaction of FAK and β4 integrin by using a site-directed mutagenesis approach to convert individual amino acids into alanine.

Accordingly, the present invention provides an agent for treatment or prevention of a cancer, which is selected from the group consisting of (1) a peptide derived from FAK, containing at least Glu$^{380}$-Lys$^{381}$-Gln382, or a mimetic peptide thereof; such as FAK/3aa (the 380$^{th}$ to 382$^{th}$ amino acids of FAK, SEQ ID NO: 1), FAK/I11aa (the 376$^{th}$ to 386$^{th}$ amino acids of FAK, SEQ ID NO: 2), FAK/25aa (the 376$^{th}$ to 400$^{th}$ amino acids of FAK, SEQ ID NO: 3) or the full length of the amino acids of FAK (FAK/400aa, SEQ ID NO: 4);

(2) a peptide derived from of β4 integrin, e.g., cytodomain of β4 integrin (the 796$^{th}$ to the 1190$^{th}$ amino acids of β4 integrin, SEQ ID NO: 5);

(3) an agent for gene therapy, which is a polynucleotide coding for an amino acid fragment of FAK containing at least FAK/3aa, such as a 9-nucleotide molecule (a molecule containing 9 nucleotides coding for coding for FAK/11aa (SEQ ID NO: 6), a 33-nucleotide moledule coding for FAK/11aa (SEQ ID NO: 7) or a 75-nucleotide molecule coding for FAK/25aa (SEQ ID NO: 8);

(4) an antibody against a peptide derived from FAK, containing at least Glu$^{380}$-Lys$^{381}$-Gln$^{382}$, such as FAK/3aa (SEQ ID NO: 1), FAK/11aa (SEQ ID NO: 2), FAK/25aa (SEQ ID NO: 3) or FAK/400aa (SEQ ID NO: 4); or an antibody which is generated against a peptide derived from cytodomain of β4 integrin, e.g., cytodornain (the 796$^{th}$ to the 1190$^{th}$ amino acids, SEQ ID NO: 5) of β4 integrin; or (5) a compound which blocks the binding of β4 integrin and focal adhesion kinase (FAK).

The present invention is explained in the above description of the invention and the following examples, which should not be used to restrict the scope of the present invention.

EXAMPLES

1. Materials and Reagents 1.1 Preparation of Plasmid DNA Construction

Full-length FAK and its various mutants, including FRNK, FAK/N375 (the first 375 amino acids), FAK/M386 (the first 386 amino acids). FAK/N400 (the first 400 amino acids), and FAK/25aa (a motif from the 375 to the 400 amino acid) were cloned, into pcDNA-3.1-Myc/6xHis, pDH-GST, and pEGFP, pHAN or pKH3 vectors to generate different tagged fusion proteins. pGEX-2T was employed to generate bacterial expression FAK constructs for GST-FAK recombinant protein purifications. The point mutants (i.e. FAKE380A/K381A/Q382A or FAKR385A/S386A) within the identified 25-amino acid motif (from amino acid 375 to amino acid 400) of FAK were generated by the overlapping PCR mutagenesis approach. The pcDNA3.1-Zeo-β4 integrin plasmid was used as a template to generate various β4 integrin mutants. In general, DNA subcloning and PCR were used to generate pcDNA-3.1-Myc/6xHis-β4 integrin, pKH3-β4/cytodomain (the 796$^{th}$ to 1190$^{th}$ amino acid), pKH3-β4 Na$^+$/Ca$^{2+}$ exchanger homologous motif (β4-CalX) and CalX-deleted (β4-deCalX) constructs for mammalian cell expression. All resulting constructs were confirmed by sequencing.

1.2 Antibodies and Reagents

Anti-FAK (C20), anti-Myc (9E10), anti-HA (12CA5), anti-GFP (B2), anti-β4 integrin (H101), and anti-tubulin were purchased from Santa Cruz Biotechnology (Santa Cruz, Calif., USA). Anti-SAPK/JNK, anti-phospho-SAPK/JNK (Thr183/Tyr185), anti-ERK1/2, anti-phospho-ERK (pT202/pY204), anti-p38 MAPK (N20), anti-phospho-p38 MAPK (Thr180/Tyr182), anti-AKT, and anti-phospho-AKT (S473) antibodies were obtained from Cell Signaling (Danvers, Mass.). Additionally, anti-phospho-FAK (Y397) antibody was from Invitrogen, anti-GST antibody was from Upstate (Charlottesville, Va.), and anti-phospho-paxillin (Tyr118) and anti-paxillin antibodies were from BD (Becton, Dickinson and Company). The FAX inhibitor PF-573, 228 was purchased from Tocris Bioscience (Ellisville, Mo.).

2. Statistical Analysis

Student's t-test was used for statistical analyses. The data in this study are presented as the mean and error bars represent the standard deviation. The data were acquired from at least three independent experiments. *, p<0.05 was considered significant differences among the experimental groups. Spearman's γ correlation test was used to assess the relationship between β4 integrin and FAK.

3 Experiment on the Contribution to Malignancy of Breast Cancer 3.1 Samples and Methods 3.1.1 Human Tissue Samples A tissue microarray containing 48 paraffin-embedded human triple-negative breast cancer samples (BRC964) was purchased from Pantomics, Inc. (Richmond, Calif.). The surgical specimens of primary cancerous breast tissues and surrounding non-cancerous breast tissues that were used for Western blotting and immunoprecipitation analysis were obtained from four patients who were not given preoperative chemotherapy and who had undergone resection with curative intent between September 2010 and December 2013 at National Taiwan University Hospital (Taipei, Taiwan). All tissues were collected with informed consent according to the Institutional Review Board of National Taiwan University Hospital (Taipei, Taiwan). All experimental protocols in this study were approved by the National Taiwan University Hospital Research Ethics Committee and were carried out in accordance with the Institutional Review Board of National Taiwan University Hospital (Taipei, Taiwan).

3.1.2 Immunohistochemical Analysis

Paraffin embedded human cancer samples were sectioned and stained after antigen retrieval using primary antibodies against FAK (C20, 1:200) and integrin (H101, 1:200), followed by a biotinylated and peroxidase-conjugated secondary antibody. The sections were processed by using a DAB immunostaining assay kit (DAKO, Glostrup, Denmark) according to the manufacturer's instructions. The samples were further counterstained with hematoxylin before mounting on coverslips. They were then examined under a fluorescence microscope (Model M1, Zeiss, Germany) with a 10× or 40+ objective lens, and the images were captured using a CCD camera (DP71, Olympus, Japan). The level of staining was scored by Quick-score (Q-score) method based on the staining intensity and the percentage of tumor cells with positive staining. The staining intensity was scored as 0, 1, 2, or 3 corresponding to negative, weak, moderate, or strong, respectively. The percentage of tumor cells positively stained was scored as 0, 1, 2, 3, or 4 corresponding to 0% 1-25%, 26-50%, 51-75%, or 76-100%, respectively. The Q-score of each tissue sample was the sum of the staining intensity and the percentage of tumor cells with positive staining. The score range was from 0 to 7. A Q-score>2 was defined as overexpressed or positive expression, and a Q-score<2 was defined as normal or negative expression.

3.1.3 Cell Culture and Transfection

MCF7 human breast cancer, MDA-MB-231 human breast cancer, MDA-MB-435 human melanoma, and 293T human epithelial kidney cell lines were maintained in Dulbecco's modified Eagle's medium (DMEM) supplemented with 10% fetal bovine serum (FBS) (Invitrogen). MCF10A normal mammary epithelial cells were cultured in Medium-171 containing MEDS (Life Technologies). Mouse fibroblast NIH3T3 cells were cultured in DMEM medium containing 10% calf serum (Invitrogen). All cells were incubated in a 37° C. humidified 5% $CO_2$ incubator. Cells were transfected with mammalian expression plasmids, as indicated, using Lipofectamine 2000™ transfection reagent (Invitrogen) according to the manufacturer's instructions. Experiments were conducted 24-48 h after transfection.

3.1.4 Immunofluorescence Staining

The cells were processed for immunofluorescence staining. In the EGF-stimulated condition, cells were treated with 10 ng/ml EGF for 10 min after overnight serum starvation. The primary antibodies used were polyclonal anti-FAK (C20, 1:200) and monoclonal anti-β4 integrin (3E1, 1:200). Alexa Fluor 488-conjugated goat anti-rabbit IgG and Texas Red-conjugated goat anti-mouse IgG were used as the secondary antibodies. Cell nuclei were stained with DAPI for 5 min at RT. Cells were then mounted using a Slow-Fade® Light Antifade Kit (Molecular Probes, Inc.) and examined under a confocal laser scanning microscope (LSM 780, ZEISS) with a 63× objective lens.

3.1.5 Western Blotting and Immunoprecipitation

Various plasmid-transfected or pharmacologically treated cells or tissue samples were homogenized and extracted for Western blot analyses. About 10-20 μg whole cell lysate were used for Western blotting. A 1 mg/ml concentration of total protein from cell lysates was employed for immunoprecipitation. Some extracts subjected to immunoprecipitation were incubated with antibodies, as indicated, for 4 h at 4° C., followed by incubation for 4 h or overnight with protein A-Sepharose 4B or protein G-Sepharose beads (Sigma-Aldrich) before proceeding to Western blot analysis. Each experiment was repeated at least three independent times.

3.1.6 Preparation of Recombinant Fusion Proteins

The constructs were transformed into a BL21 strain and grown at 37° C. until at an optical density at 600 nm of 0.6. They were then induced with 1 mM isopropyl-β-thiogalactopyranoside overnight at 26° C. Subsequently, cells were pelleted and resuspended with PBS following sonication with a Misonix sonicator 3000. Then, Triton X-100 (1%) was added and cells were incubated on ice for 1 h. The lysates were clarified by centrifugation and then immobilized on GST-agarose beads (Sigma-Aldrich) or Nickel-nitrilotriacetic agarose (Ni-NTA. Qiagen) for 6 h at 4° C. Finally, the beads were washed and then eluted.

3.1.7 Lentivirus Production and Infection

Lentiviruses encoding ITGB4 small-hairpin RNAs (shRNA) or LUCIFERASE small-hairpin RNA was obtained from the TRC lentiviral shRNA library in the National RNAi Core Facility of Academia Sinica, Taiwan. The targeting sequences of specific shRNAs are shown as follows: ITGB4 shRNA (clone ID: TRCN0000057769) 5'-CCCATGAAGAAAGTGCTGGTT-3', ITGB4 shRNA (clone ID: TRCN0000057771) 5'-GAGGGTGTCATCAC-CATTGAA-3', and LUCIFERASE shRNA (clone ID: TRCN0000072246) 5'-CAAATCACAGAATCGTCGTAT-3'. Production of lentiviruses was performed according to the guidelines of the National RNAi Core Facility of Academia Sinica.

3.1.8 BrdU Incorporation Assay

At 24 h after transfection, $2\times10^4$ cells were serum starved for 24 h. Cells were then washed twice with DMEM and incubated for 16 h in DMEM plus 10% FBS and 100 μM BrdU (Sigma-Aldrich). After that, cells were fixed, permeabilized, heated with DNase I, and processed for immunofluorescence staining, with anti-BrdU (1:200, Sigma-Aldrich) antibody, as described previously[39], with a few modifications. Cells were then counted in multiple fields and scored for BrdU-positive staining in each independent experiment.

3.1.9 Anchorage-Independent Growth in Soft Agar Assay

Experiments were performed as previously described[39], with the following modifications. A total of $5\times10^4$ cells were seeded in 0.3% agar in DMEM plus 10% PBS and EGF (10 ng/ml) over the bottom 0.6% agar layer in DMEM. After incubation for 14 days, the number of colonies was scored.

3.1.10 Modified Boyden Chamber Cell Migration Assay

A Neuro Probe 48-well chemotaxis Boyden chamber (Cabin John, Md.) was used. A total of $5\times10^4$ cells were allowed to migrate toward 10% FBS, EGF (10 ng/ml) in DMEM, used as the chemoattractant in the lower wells for 6 h. Finally, cells on the upper side of the polycarbonate membrane were removed and the bottom-side cells were fixed with methanol for 8 min and stained with crystal violet (Sigma-Aldrich). The migrated cells were counted from five randomly selected fields of each well.

3.1.11 Matrigel Invasion Assay

BD BioCoat™ Matrigel™ invasion chambers were rehydrated by DMEM for 2 h. After removing the DMEM, EGF (10 ng/ml), and 10% FBS in DMEM was used as a chemoattractant in the lower wells of the invasion chamber. A total of $56\times10^4$ cells in DMEM were placed into the upper chamber. Cells were incubated for 20 h to allow them to invade into the Matrigel. Subsequently, cells were fixed with 4% paraformaldehyde for 15 min and stained with crystal violet (Sigma-Aldrich). The number of invaded cells was counted from five randomly selected fields in each welt 3.1.12 Modeling Tumorigenesis and Metastasis In Vivo All mouse experiments were approved by the Institutional Animal Care and Use Committee, National Taiwan University (Taipei, Taiwan). All experimental procedures were performed in accordance with the protocols and the ethical regulations approved by the Institutional Animal Care and Use Committees of National Taiwan University (Taipei, Taiwan). Female nu/nu mice were purchased from the National Laboratory Animal Center (Taipei, Taiwan). For tumorigenesis, $1\times10^6$ MDA-MB-231 stably transfected pools expressing GFP-tagged FAK/25aa, its triple (FAK/25aa$^{E380A/K381A/Q382A}$) or double (FAK/25aa$^{R385A/S386A}$) mutant, or a mock transfected control that had been selected by 500 μg/ml G418 for 2 weeks were injected into the 3$^{rd}$ mammary fat pad of eight-week-old female nu/nu mice. Stably transfected pools of each construct were injected in 100 μl PBS. Tumor volumes and numbers were measured at 12 weeks after injection and then excised, photographed, and weighted. For tumor metastasis, $1\times10^6$ MDA-MB-231 cells, described above, that were labeled with luciferase by lentiviral infection were resuspended in 100 μl PBS and injected into the tail vein of six-week-old female nu/nu mice. Lung metastasis was monitored by bioluminescent imaging using an IVIS spectrum imaging system. Lung metastasis was measured on the respective day after injection.

3.1.13 Preparation of TAT-FAK 2.5aa Peptide

TAT and TAT-FAK/25aa peptides were synthesized. The sequences of TAT and TAT-FAK/25aa peptides were GRKKRRQRRRPQ (SEQ ID NO: 9) and GRKKRRQRRRPQLANNEKQGVRSHTVSVSETD-DYAE1 (SEQ ID NO: 3), respectively. Purity of synthesized peptides was confirmed by high-performance liquid chromatography (HPLC).

3.2 Result

3.2.1 The physical interaction between β4 integrin and FAK correlates with tumor malignancy.

Figure 1B:
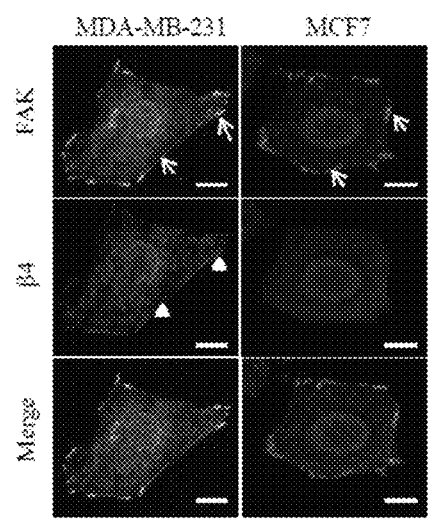
FIG. 1(b) shows that MDA-MB-231 (aggressive) and MCF7 (non-aggressive) cells were stained to show the co-localization of FAK (green, arrows) and β4 integrin (red, arrowheads) on the peripheral plasma membrane in MDA-MD-231 cells but not in MCF7 cells. Scale bars, 10 μm.

The putative interaction between β4 integrin and FAK in relation to tumor malignancy was analyzed by immunoprecipitation in varied cancer cell lines. The interaction between β4 integrin and FAK was identified in the malignant triple-negative breast cancer cell line (MDA-MB-231) (FIG. 1(a)) as well as in the metastatic colon cancer cell line (HCT-116) (unpublished data), but not in the non-tumorigenic breast epithelial cell line (MCF10A) or other cancer cell lines (i.e., MCF7, MDA-MB-435, A549, and HeLa). In addition, we also observed that β4 integrin and FAK were co-localized in the plasma membrane or protrusions of metastatic breast MDA-MB-23I cells in contrast to that observed in the non-metastatic breast MCF7 cells (FIG. 1(b)). Together, these results indicate that β4 integrin might interact with FAK in MDA-MB-231 breast cancer cells.

Figure 1C:
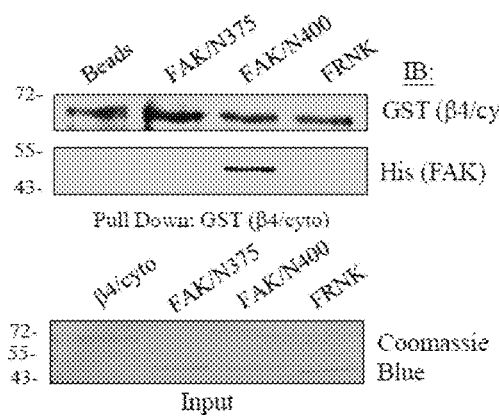
FIG. 1(c) shows that the association between β4 integrin and FAK-derived recombinant proteins was determined by an in vitro binding assay.
Figure 1D:
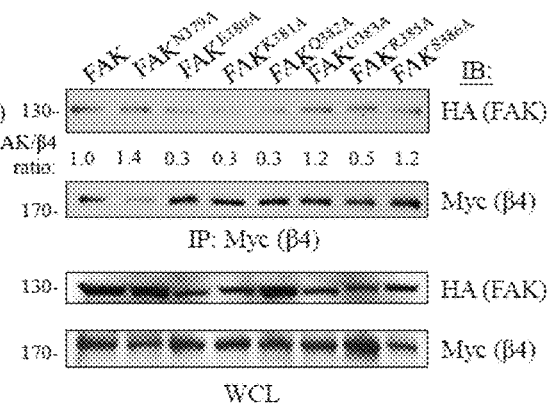
FIG. 1(d) shows that by immunoprecipitation and Western blot analysis, the crucial amino acids that were responsible for interaction with β4 integrin were determined. The mean of the relative interaction between β4 integrin and FAK (normalized to wild-type FAK shown as 1.0) was measured.
Figure 1E:
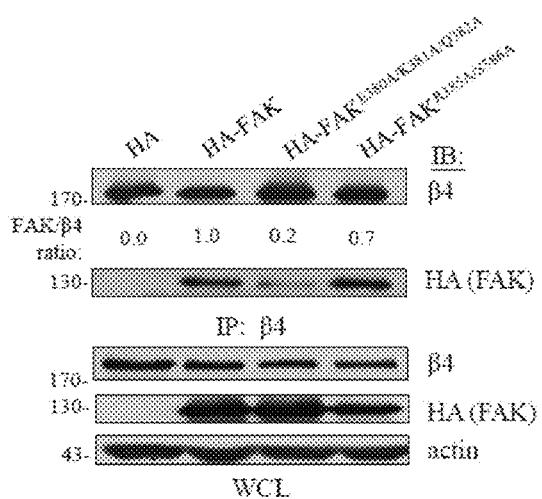
FIG. 1(e) shows that the triple amino acids ($FAK^{E380A/K381A/Q382A}$) exhibited a marked reduction in β4 integrin binding compared to wild-type FAK or the double (FAK$^{R385A/S386A}$) mutant.
Figure 1F:
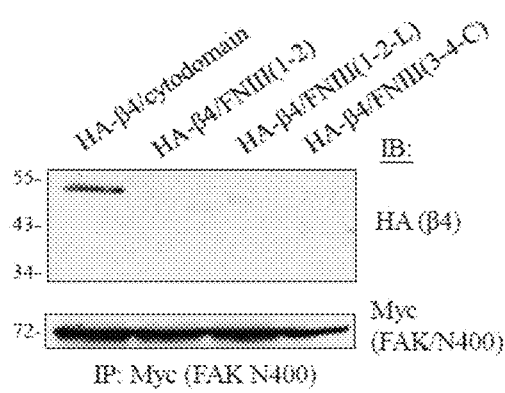
FIG. 1(f) shows that the cytodomain of β4 integrin is indispensable to its interaction with FAK. Each experiment was repeated at least three independent times. All cropped blots were run under the same experimental conditions.
Figure 1G:
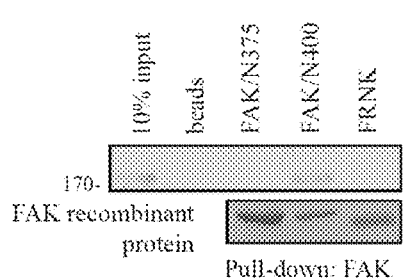
FIG. 1(g) shows the results in which the cell lysates from MDA-MB-231 cells which were incubated with the His-tagged FAK amino- (i.e. FAK/N375 and FAK/N400) or carboxyl—(i.e. FRNK) recombinant proteins (were shown on the bottom by Coomassie blue staining) and subsequently, His-tagged proteins were pulled down by Ni-conjugated beads, and followed by Western blotting with anti-β4 integrin antibody.
Figure 1H:
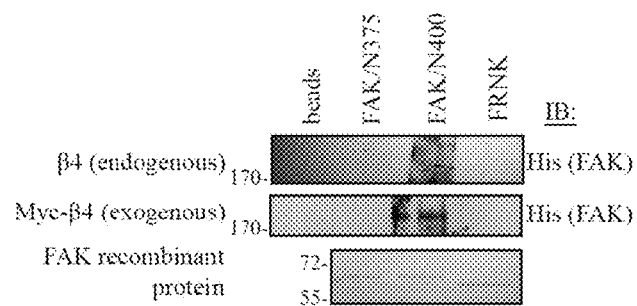
FIG. 1(h) shows that the capability of FAK binding directly to β4 integrin in the far-Western assay, in which immunoprecipitated β4 integrin obtained from MDA-MB-231 endogenous β4 integrin (endogenous) or ecotopic expression Myc-tagged β4 integrin (exogenous) was subjected to SDS-PAGE and then transferred onto nitrocellulose membranes: and renatured β4 integrin protein by removing SDS was incubated with the purified His-tagged FAK amino- or carboxyl-recombinant proteins, as indicated (were shown on the bottom by Coomassie blue staining) then Western blotting with anti-His antibody against FAK proteins.

To clarify the physical interaction between β4 integrin and PAK, we demonstrated that the recombinant His-tagged FAK/N400 was capable of precipitating β4 integrin from MDA-MB-231 cells, but neither His-tagged FAK/N375 nor His-taged FRNK (FIG. 1(g)). Using the far-Western assay and the in vitro pull-down assay, we further evidenced a direct interaction between β4 integrin and FAK, requiring the first 400 amino acids of FAK (but not within the first 375 amino acids) and the cytodomain of β4 integrin (FIG. 1(c) and FIG. 1(h)). Together, these results support, for the first time, a physical link between the cytodomain of β4 integrin and the 25-amino-acid motif within the FAK's N-terminus present in triple-negative breast cancers.

Figure 1I:
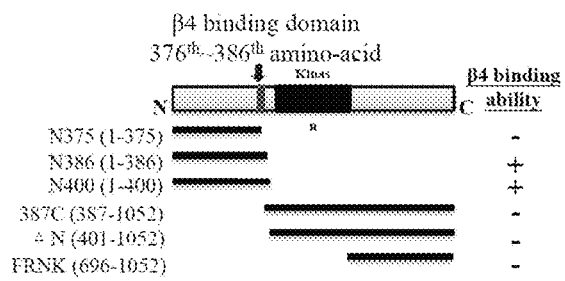
FIG. 1(i) shows a summary of various FAK truncated mutants capable of interaction with β4 integrin is listed.
Figure 1J:
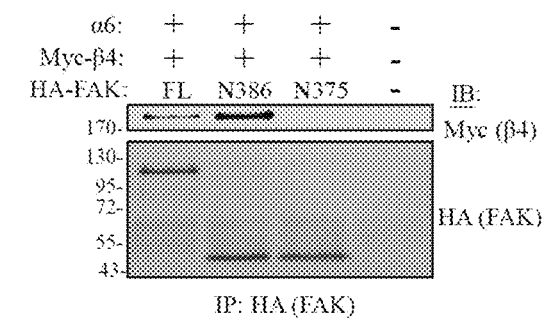
FIG. 1(j) shows the results, in which HEK293 cells were co-transfected with Myc-tagged integrin α6β4 and HA-tagged full-length FAK or its amino-terminal fragments, i.e. FAK/N386 and FAK/N375, cell lysates were immunoprecipitated by anti-HA antibody against FAK or its mutants, and the co-immunoprecipitated β4 integrin was visualized by anti-Myc antibody; indicating that the 376th to the 386th amino acids within FAK is capable of binding with β4 integrin.
Figure 1K:
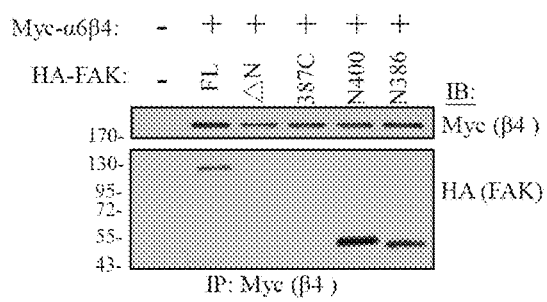
FIG. 1(k) shows that HEK293 cells were co-transfected with Myc-tagged integrin α6β4 and HA-tagged full-length FAK or its amino-terminal deletion mutants (i.e. FAK/ΔN, FRNK and FAK/387C), amino-terminal fragments (i.e. FAK/N400 and FAK/N386) and cell lysates were collected and immunoprecipitated by anti-Myc antibody against β4 integrin.
Figure 1L:
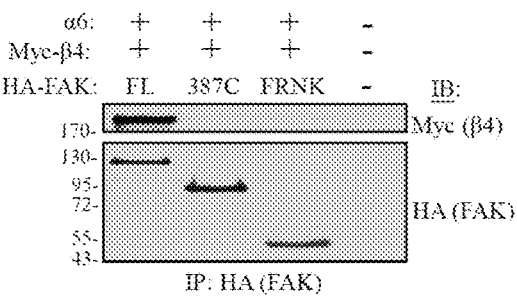
FIG. 1(l) shows that HEK293 cells were co-transfected with Myc-tagged integrin α6β4 and HA-tagged full-length FAK or its amino-terminal deletion mutants (i.e. FAK/ΔN, FRNK and FAK/387C), amino-terminal fragments (i.e. FAK/N400 and FAK/N386) and cell lysates were collected and immunoprecipitated by anti-Myc antibody against anti-HA antibody against FAK.

In light of the above findings, we further dissect the binding sites for these two molecules. Firstly, we generated a serial FAK truncated mutants to be subjected for co-immunoprecipitation with β4 integrin. Collectively, as summarized in FIG. 1i we found that an 11-amino-acid region (i.e., from the $376^{th}$ to the $386^{th}$) ahead of the FAK-$Tyr^{397}$ autophosphorylated site is responsible for β4 integrin binding (FIG. 1(j)-FIG. 1(l)). Furthermore, we mapped the essential amino acids of the 11 amino acids, $Leu^{376}$-Ala-Asn-Asn-Glu-Lys-Gln-Gly-Val-Arg-$Ser^{386}$, critically involved in the interaction with β4 integrin using a site-directed mutagenesis approach to convert individual amino acid into alanine. As a result, three ($Glu^{380Ala}$, $Lys^{381Ala}$, and $Gln^{382Ala}$) out of 10 alanine mutants of FAK significantly diminished the binding capability with β4 integrin in comparison to that of the wild-type FAK (FIG. 1d). Then, we generated and tested the β4 integrin binding ability of the triple-point-mutation mutant, i.e. $FAK^{E380A/K381A/Q382A}$, and the control double-point-mutation mutant, i.e. $FAK^{R385A/S386A}$, of FAK, consistently supporting the essential role of the $Glu^{380th}$, $Lys^{381st}$, and $Gln^{382nd}$ for interaction with β4 integrin (FIG. 1(e)).

Figure 1M:
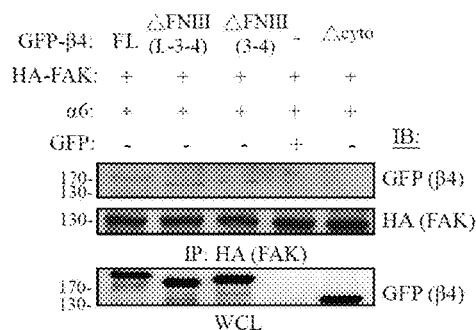
FIG. 1(m) shows that HEK293 cells were co-transfected with HA-tagged FAK, Myc-tagged α6 integrin and CFP-tagged β4 integrin full-length or its various cytoplasmic domain deletion mutants to determine the FAK binding domain within β4 integrin; and cell lysates were collected and immunoprecipitated by anti-HA antibody against FAK, co-immunoprecipitated β4 integrin fragments were visualized by anti-CFP antibody.
Figure 1N:
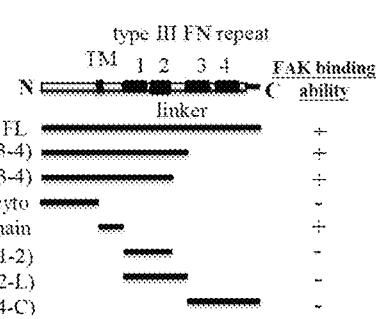

On the other hand, we sought for the FAK binding site on β4 integrin by co-immunoprecipitation using distrinctive regions derived from the β4 integrin cytoplasmic domain, such as the cytodomain, the FNIII(1-2), the FNIII(1-2-L), and the FNIII(3-4-C). Collectively, as summarized in FIG. 1n, we determined the FAK binding site of β4 integrin resided on the cytodotnain of β4 integrin, where is proximal to the plasma membrane rather than the FNIII repeats or the linker region (FIG. 1(f) and FIG. 1(m)).

3.2.2 EGF/Sre Signaling Regulates β4 Integrin Phosphorylation and Integrin/FAK Complex Formation.

Figures 2A, 2B, 2C:
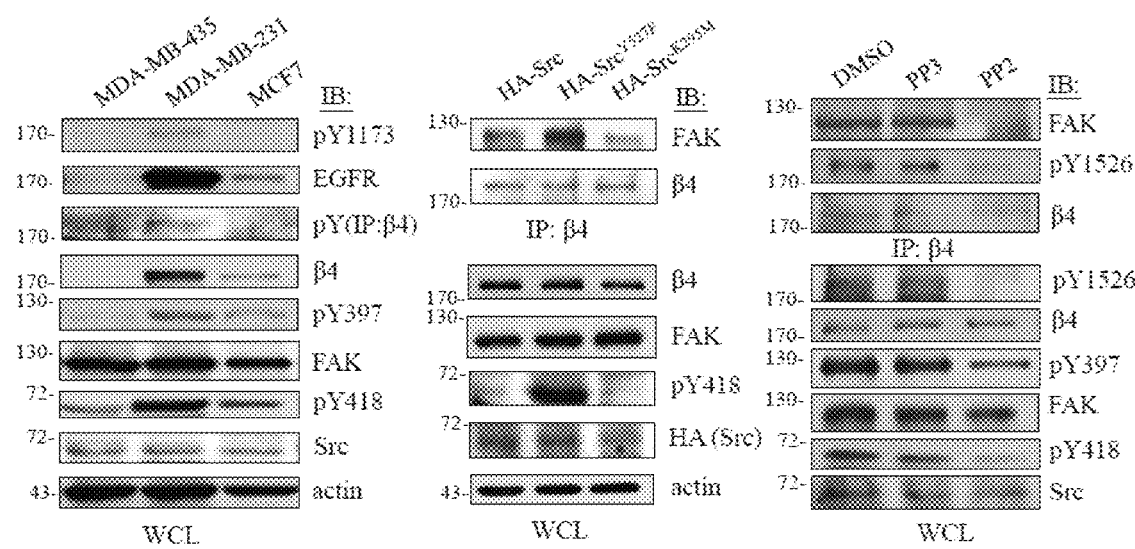
FIGS. 2(a)-2(f) show the EGF/Sre-dependent β4 integrin phosphorylation modulates the formation of the β4 integrin/FAK complex.

The discrepancy between metastatic MDA-MB-231 cells and non-metastatic MCF7 cells in the β4 integrin/FAK complex formation prompted us to investigate the regulatory mechanisms involved in the formation of this complex. We observed that EGFR autophosphorylation at $Tyr^{1173}$, Src phosphorylation at $Tyr^{418}$, tyrosine phosphorylation of β4 integrin, and FAK autophosphorylation at $Tyr^{397}$ were more prevalent in MDA-MB 231 cells compared to MCF7 cells (FIGS. 1(a) and 2(a)), implying that a tyrosine phosphorylation cascade through EGF/Src-family kinases (STKs) is associated with β4 integrin/FAK complex formation. To explore this possibility, we directly tested the role of Src kinase activity on β4 integrin/FAK complex formation. First, we found that the interaction between β4 integrin and FAK was elevated in the presence of constitutively active $Src^{Y527F}$ compared to the wild-type or kinase dead ($Src^{K295M}$) Src-expressing MDA-MB-231 cells (FIG. 2(b)). In accordance with this finding, the formation of the β4 integrin/FAK complex was markedly reduced in the presence of PP2, an Src kinase inhibitor, compared to PP3- or DMSO-treated cells (FIG. 2(c)). Moreover, the phosphorylation levels of β4 integrin at $Tyr^{1526}$ and FAK at $Tyr^{397}$ were also reduced upon blocking Src kinase activity. Indeed, we revealed that two ($Tyr^{1526}$ and $Tyr^{1642}$) out of five potential SPK-mediated tyrosine phosphorylation sites in the β4 integrin signaling domain were intimately associated with the formation of the β4 integrin/FAK complex (FIG. 2(d)). Collectively, these results show that Src kinase activity is involved in the interaction between β4 integrin and FAK.

Figures 2D, 2E, 2F:
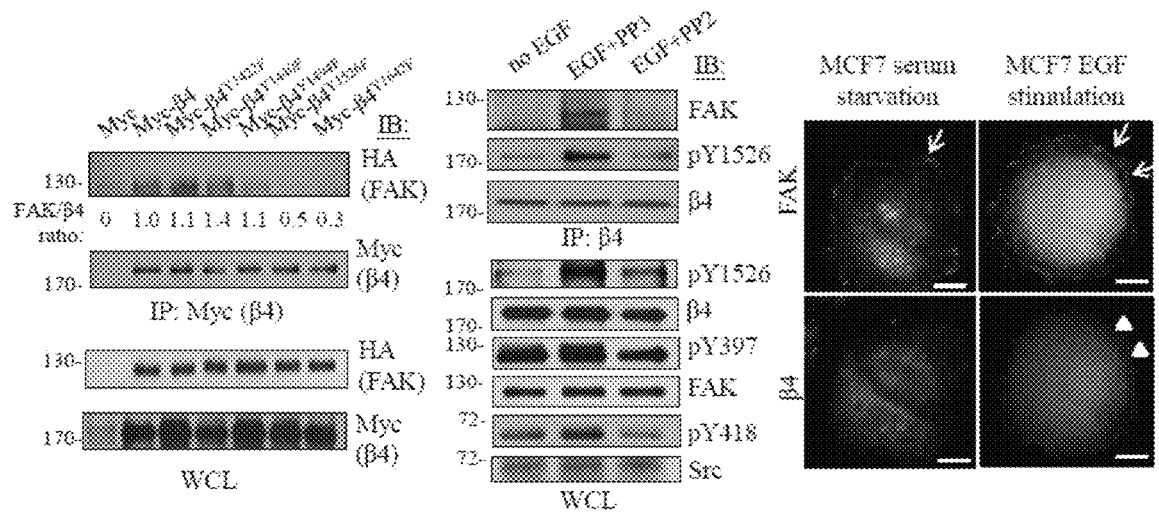

Tyrosine phosphorylation of β4 integrin by SFKs is reportedly important for the progression of tumor malignancy in a growth factor-dependent manner. We next attempted to determine whether EGF/EGFR signaling enables the control of Src-mediated the β4 integrin/FAK complex formation. As shown in FIG. 2(e), the interaction, between β4 integrin and FAK was virtually increased by EGF stimulation but remained absent in the presence of PP2, indicating that EGF/Src-mediated signaling was involved in the β4 integrin/FAK complex formation. In accordance with the tyrosine phosphorylation regulatory cascade, we also observed that the tyrosine phosphorylation of β4 integrin and FAK was also affected by EGF/Src-mediated signaling. Moreover, upon EGF stimulation, the concomitant increases in Src phospho-$Tyr^{418}$, β4 integrin phospho-$Tyr^{1526}$ and FAK phospho-$Tyr^{397}$ coincided with the co-localization in the plasma membrane of β4 integrin and FAK in MCF7 cells (FIG. 2(f)). Moreover, the same phenomenon was investigated in EGF-stimulated MDA-MB-231 cells, which showed the same co-localization at plasma membrane of β4 integrin and FAK. Taken together, our findings revealed that an intrinsic phospho-tyrosine cascade that is triggered by an EGF/Src-mediated signaling enables transduction through the β4 integrin/FAX complex.

Figure 3A:
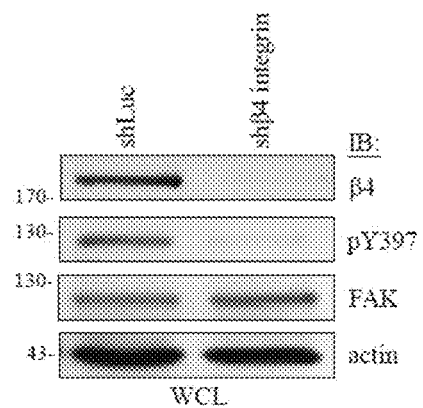
FIG. 3(a)-3(e) show the interaction with β4 integrin leads to the activation of FAK and its downstream signaling.
Figure 3B:
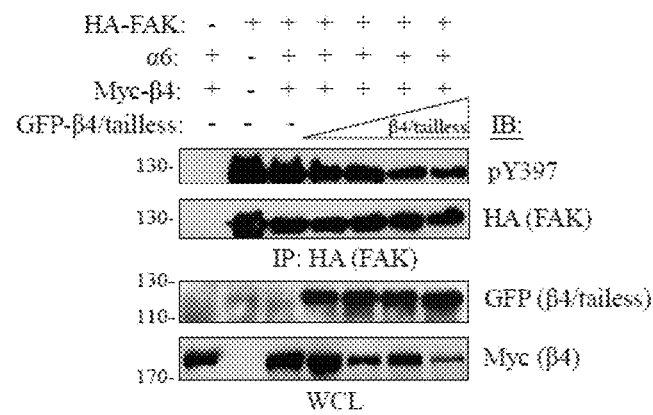
Figure 3C:
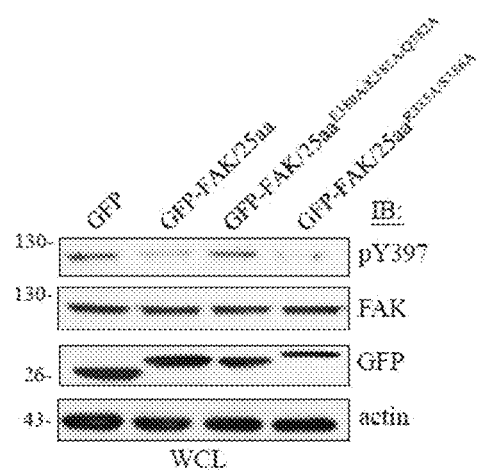
Figure 3D:
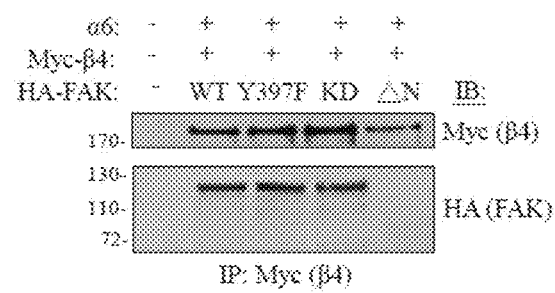

3.2.3 Interaction with β4 Integrin Enhances the Activity and Downstream Signaling of FAK The downstream effects of the β4 integrin/FAK complex on breast cancer malignancy were then investigated. We noticed that the β4 integrin that co-immunoprecipitated with FAX was predominately phosphorylated at $Tyr^{397}$ (FIG. 1(a)). Hence, we speculated a novel activation mechanism for FAX that included an interaction with β4 integrin via the linker motif ahead of the $Try^{397}$ of FAX. Consistent with this, in β4 integrin knockdown cells that were deprived of the phosphorylation of FAX (FIG. 3(a)), the level of FAX phospho-$Tyr^{397}$ decreased in accordance with increasing β4 integrin/tailless mutant, which can compete with full-length β4 integrin to interact with α6 integrin (FIG. 3(b)), due to the loss of FAX bound to β4 integrin. To further support this observation, we attempted overexpressing the FAK/25aa peptide (the $376^{th}$ to the $400^{th}$ amino acid), the motif for FAX that binds to β4 integrin (FIG. 1), to compete and disrupt β4 integrin/FAK complex formation in a dose-dependent manner (FIG. 4(a)). Meanwhile, the triple (FAX/25aa$^{E380A/K381A/Q382A}$) and double (FAX/25aa$^{R385A/S386A}$) FAK/25aa peptide mutants were used as controls. As expected, we found that FAX phospho-Tyr$^{397}$ was decreased in FAK/25aa- and FAK/25aa$^{R385A/S386A}$-transfected cells in comparison to mock or FAX/25aa$^{E380A/K381A/Q382A}$-transfectants (FIG. 3(c)). In accordance, the β4 integrin/FAK complex formation was indispensable to FAX activation due to the fact that the FAX$^{Y397F}$ or kinase dead (FAK$^{K454M}$) mutant of FAX retained the ability to bind with β4 integrin (FIG. 3(d)).

Next, several potential downstream signaling targets were examined to test whether any of them participates in β4 integrin/FAK complex-mediated cancer functions. As a result, AKT and p38MAPK were revealed to participate in β4 integrin/FAX complex-mediated signal transduction in triple-negative breast cancer (FIG. 3(e)). Collectively, these results suggest that β4 integrin enables the physical recruitment and subsequent activation of FAX, which promotes AKT and p38MAPK signaling in an EGF/Src dependent manner, thereby regulating breast cancer malignancy.

3.2.4 The β4 Integrin/FAK Complex Leads to Tumor Malignancy In Vitro.

The involvement of β4 integrin FAK, in tumor malignancy is well documented. Thus, along with our findings, overexpression of FAK/25aa, which decreases β4 integrin/FAK complex formation and FAK activation (FIG. 3), allowed us to examine the biological effects of the β4 integrin/FAK complex. As expected, the level of FAK co-immunoprecipitated by β4 integrin was attenuated in a dose-dependent manner that correlated with increased expression of FAK/25aa (FIG. 4(a)). Conversely, the amounts of FAK/25aa co-immunoprecipitated by β4 integrin were increased, indicating that the reduction of the β4 integrin/FAK complex is a result of FAK/25aa competing with full-length FAK to bind with β4 integrin. It should be noted that the specificity of FAK/25aa in influencing the β4 integrin/FAK complex was affirmed because the paxillin/FAK complex and β1 integrin-mediated cell migration were not affected when FAK/25aa was overexpressed in NIH3T3 cells.

Then, we performed various functional assays to evaluate the role of the β4 integrin/FAK complex in tumor malignancy in MDA-MB-231 cells. We found that cell proliferation was decreased in FAK/25aa and the FAK/25aa$^{R385A/S386A}$ transfectants compared to mock and the FAK/25aa$^{E380A/K381A/Q382A}$-transfected cells (FIG. 4(b)), implicating the β4 integrin/FAK complex in promoting cancer cell proliferation. In addition, the β4 integrin/FAK complex had a profound impact on enhancing the anchorage-independent growth of MDA-MB-231 cells (FIG. 4(c)). Concurrent with the critical role of FAK in cell migration, the β4 integrin/FAK complex had a progressive effect on cell migration toward fetal bovine serum (FBS) or EGF (FIG. 4(d)). In agreement with the above, the β4 integrin/FAK complex clearly participated in tumor invasion in MDA-MB-231 cells (FIG. 4(e)). Collectively, the β4 integrin/FAK complex serves is a crucial candidate for identifying breast cancer malignancies.

Figure 3E:
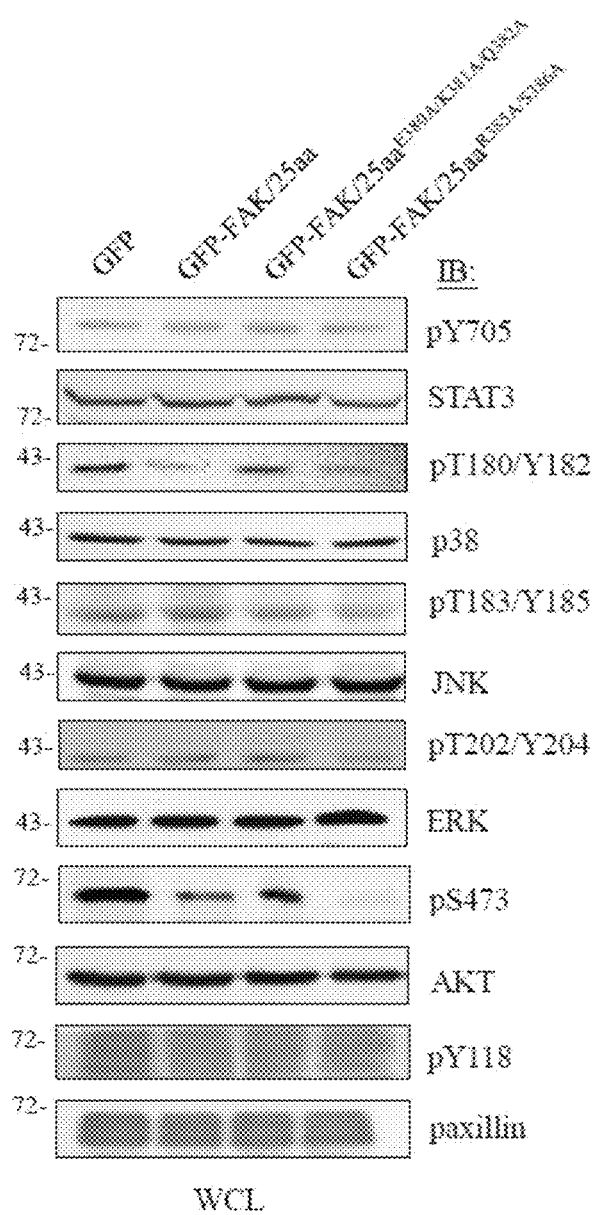

Given that the β4 integrin/FAK complex enables the activation of AKT- and p38MAPK-mediated signaling (FIG. 3(e)), the distinct role of AKT and p38MAPK β4 integrin/FAK complex-mediated cancer malignancy was investigated. By using pharmacological inhibitors, i.e., an AKT inhibitor (AKT-in) and a p38MAPK inhibitor (SB203580), we found that AKT, but not p38 MAPK, is involved in β4 integrin/FAK complex-mediated anchorage-independent growth under EGF-stimulated conditions. On the other hand, p38MAPK was required for cell migration toward EGF. Taken together, our data reveals the molecular mechanism through which an intrinsic tyrosine phosphorylation cascade of the EGF/Src-mediated β4 integrin/FAK complex is involved in the development of breast cancer malignancy.

3.2.5 The β4 Integrin/FAK Complex is Involved in Tumor Malignancy In Vivo.

Figure 5A:
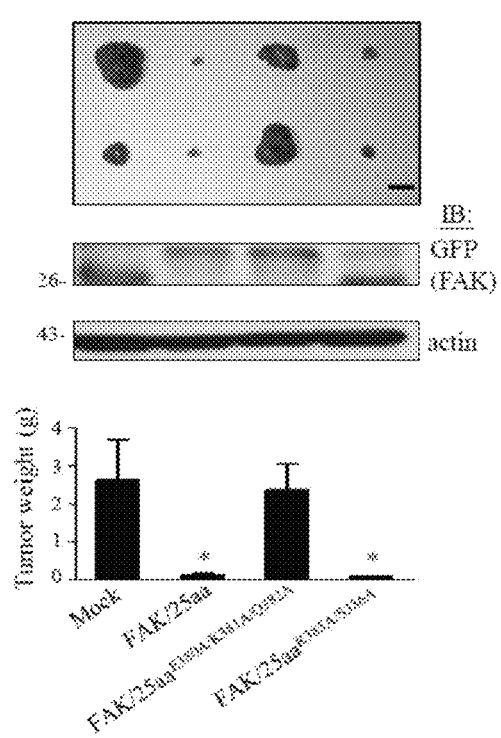
FIGS. 5(a)-5(c) show the β4 integrin/FAK complex regulates tumor malignancy in vivo.

To confirm the tumorigenic effects of the β4 integrin/FAK complex we observed in the above in vitro studies, we performed in vivo tumorigenesis studies by orthotopically injecting MDA-MB-23 I cells that stably overexpressed varied FAK/25aa mutants into the mammary fat-pads of nude mice. Mice injected with stably expressing FAK/25aa or FAK/25aa$^{R385A/S386A}$ but not FAK/25aa$^{E380A/K381A/Q382A}$ transfectants of MDA-MB-231 cells showed significant reductions in the size and weight of tumors (FIG. 5(a)). Protein expression of the transfectants was sustained during tumor growth in the transplanted mice, which reinforces an authentic role for the β4 integrin/FAK complex in breast cancer tumorigenesis.

Figure 5B:
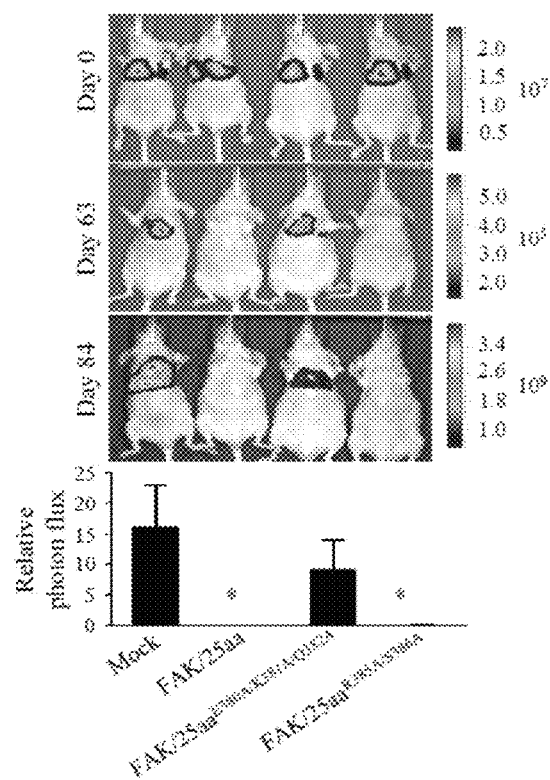
Figure 5C:
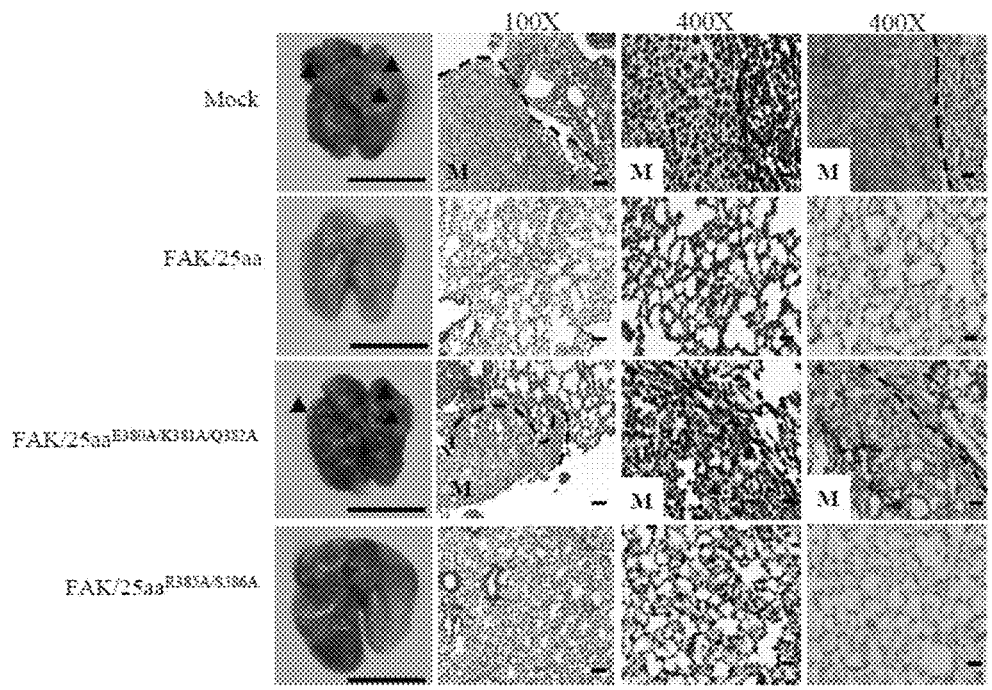
Figure 7:
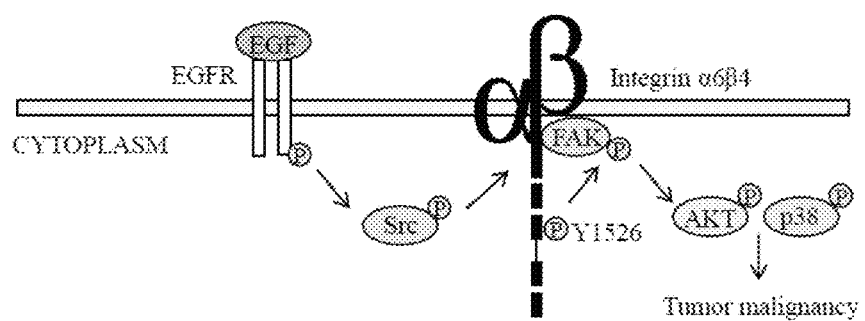
FIG. 7 shows a working model for the mechanism through which the β4 integrin/FAK complex mediates the malignancy of triple-negative breast cancer in an EGF/Src-regulated manner.

Subsequently, the involvement of the β4 integrin/FAK complex in breast cancer metastasis was explored by tail vein injection and bioluminescence imaging of various MDA-MB-231 transfectants in nude mice. In comparison with mock and FAK/25aa$^{E380A/K381A/Q382A}$-expressing cells, lung metastatic nodules were less-developed in FAK/25aa- and FAK/25aa$^{R385A/S386A}$-transfectants 84 days after injection in mice (FIG. 5(b)). In parallel, the histologic analyses confirmed the persistent presence of FAK/25aa and FAK/25aa$^{R385A/S386A}$ expression and its influence on the development of lung metastatic modules (FIG. 5(c)). These results clearly substantiate a role for the β4 integrin/FAK complex in positively regulating tumorigenesis and metastases in triple-negative breast cancer.

3.2.6 Concomitant Overexpression of β4 Integrin and FAK in Human Triple-Negative Breast Cancer.

We next analyzed the relationship of β4 integrin and FAK in four subtypes (luminal A, lumina B, HER$^{2+}$, and triple-negative) of human breast cancer (T) and their adjacent non-cancerous counterpart (N) tissues. Consistent with a malignant role for the β4 integrin/FAK complex in triple-negative breast cancer, the β4 integrin co-immunoprecipitated by FAK was predominately associated with triple-negative breast cancer compared to other subtypes (FIG. 6(a)). We further employed immunohistochemical staining in malignant triple-negative breast cancer (T) and adjacent non-cancerous (N) tissues to investigate the pathological relevance of β4 integrin and FAK. Our result indicated that concomitant expression of β4 integrin and FAK occurred in triple-negative breast cancer tissues (FIG. 6(b)), in that approximately 56% (27 out of 48) of the tumors displayed high levels of both β4 integrin and FAK, whereas approximately 17% (8 out of 48) of the tumors expressed only low levels of both proteins. Statistical results revealed a positive correlation between β4 integrin and FAK expression in these malignant cancer tissues, with a Spearman's γ correlation of 0.3772 (p=0.0082) (FIG. 6(c)). In contrast, both proteins were barely detectable in adjacent non-cancerous breast tissues (FIG. 6(h)). These observations are consistent with previous studies (FIGS. 1(a) and 2(a)) that indicated the simultaneous up-regulation of both β4 integrin and FAK and an interaction between β4 integrin and FAK that is significantly correlated to human malignant triple-negative breast cancer.

3.2.7 Targeting the Formation of the β4 Integrin/FAK Complex Potentiates the Intervention Against Triple-Negative Breast Cancer.

The FAK/25aa was fused with the TAT peptide to facilitate cellular uptake [32]. Then, the extracellular administration of the TAT-FAK/25aa peptide was apparently capable of alleviating the formation of the β4 integrin/FAK complex in MDA-MB-231 cells (FIG. 6(d), left panel). In comparison with the TAT alone, the foci of the MDA-MB-231 cells treated with the TAT-FAK/25aa peptide were approximately 30% less formed (FIG. 6(d), right panel). These results potentiate a novel strategy for triple-negative breast cancer therapeutics by targeting the formation of the β4 integrin/FAK complex.

4. Experiment on the Contribution to Malignancy of Colon Cancer

4.1 Samples and Methods

4.1.1 Human Tissue Samples from Patients Diagnosed with Colon Cancer

Patients diagnosed with colon cancer were enrolled in this study with the approval of the Institutional Review Board of National Taiwan University Hospital, Taiwan. The surgical specimens of primary colon cancer tissues and its normal mucosa counterparts were collected for Western blotting and immunohistochemical staining.

4.11 Tissue Microarray and Immunohistochemical Analyses

The human colon adenocarcinoma tissue microarray was purchased from Biomax, Inc. (MD, USA). The paraffin embedded samples were stained with antibodies against β4 integrin and FAK. The sections were processed using the DAB immunostaining kit (DAKO) according to the manufacturer's instructions. The samples were counterstained with hematoxylin, mounted, and examined. Scoring was performed according to staining intensities (0, none; +1, weak; +2, moderate; +3, strong) of β4 integrin or FAK. The results were recorded as low (0 and +1) or high (+2 and +3) intensity levels,

4.1.3 Cell Culture and Transfection

HCT-116 human colon cancer, HeLa human cervical cancer, and HEK-293 human epithelial kidney cell lines were maintained in Dulbecco's modified Eagle's medium (DMEM) supplemented with 10% fetal bovine serum (FBS) (Invitrogen). ALL cells were incubated in a 37° C. humidified 5% $CO_2$ incubator. Cell transfection was performed using Lipofectamine 2000™ reagent (Invitrogen) according to the manufacturer's instructions.

4.1.4 Western Blotting and Immunoprecipitation

Cells or tissue samples were homogenized and extracted for Western blotting. For immunoprecipitation, proteins were incubated with antibodies as indicated at 4° C. overnight, followed by incubation for 4 hrs with protein A-Sepharose 4B beads (Sigma-Aldrich). All experiments were conducted at least three independent times.

4.1.5 Preparation of Recombinant Fusion Proteins

The constructs were transformed into a BL-21 bacterial strain and grown at 37° C. until they reached an optical density at 600 nm of 0.6. They were induced with 1 mM isopropyl-β-thiogalactopyranoside overnight at 25° C. and subsequently pelleted and resuspended with PBS following sonication. The lysates were clarified by centrifugation and immobilized on GST-agarose heads (Sigma-Aldrich). The beads were washed, and proteins were eluted.

4.1.6 Lentivirus Production and Infection

Lentiviruses encoding LUCIFERASE or ITGB4 shRNAs were obtained from the TRC lentiviral shRNA library in the National RNAi Core Facility of Academia Sinica, Taiwan. The targeting sequences of specific shRNAs used are as follows: LUCIFERASE shRNA 5'-CAAAT-CACAGAATCGTCGTAT-3' (SEQ ID NO: 9), and ITGB4 shRNA 5'-CCCASGAAGAAAGTGCTGGTT-3' (SEQ ID NO: 10), 5'-GAGGGTGTCATCACCATTGAA-3' (SEQ ID NO: 11). Production of lentiviruses was processed according to the guidelines of the National RNAi Core Facility of Academia Sinica.

4.1.7 BrdU Incorporation Assay

A BrdU incorporation assay was performed. Briefly, serum-starved cells were incubated in DMEM with 10% FBS and 100 μM BrdU (Sigma-Aldrich) for 16 hrs. Cells were fixed, permeabilized, treated with DNase I, and processed for immunofluorescence staining with anti-BrdU (Sigma-Aldrich) antibody. The BrdU-positive staining cells were scored.

4.1.8 Anchorage-Independent Growth Assay

An anchorage-independent growth assay was conducted with several modifications. Briefly, $5\times10^4$ cells were seeded in a 0.3% agar in DMEM containing 10% FBS over the bottom 0.6% agar layer in DMEM. After incubation for 14 days, the number and size of colonies were scored.

4.2 Results.

Figures 8A, 8B, 8C:
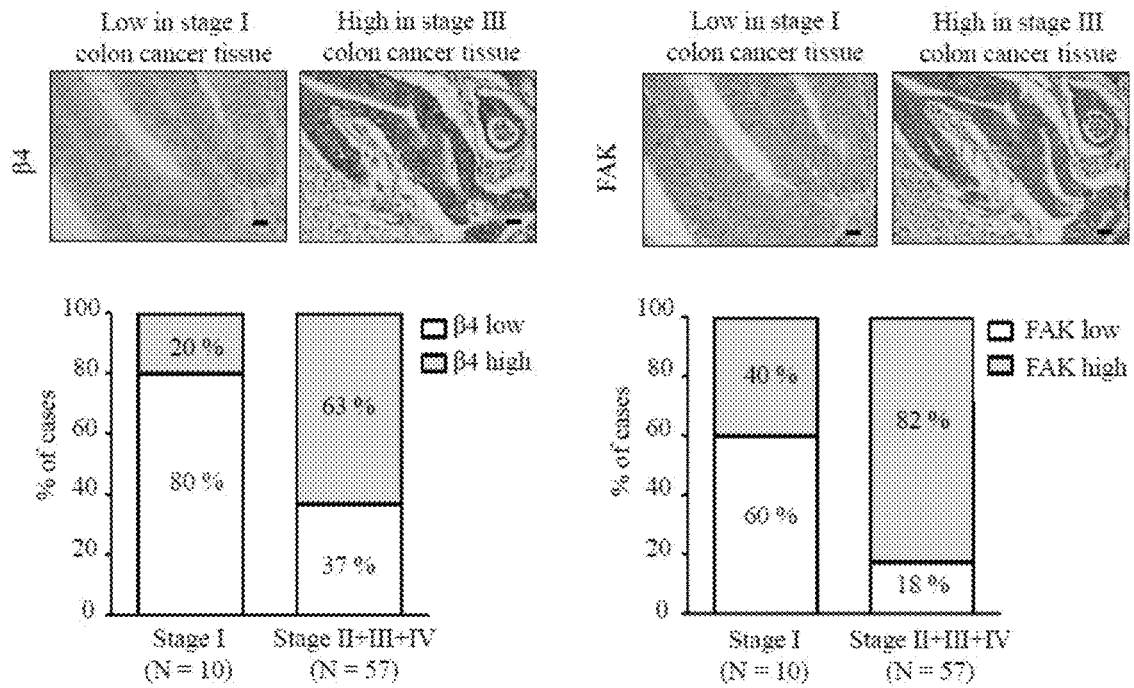
FIGS. 8(A)-8(C) show that the co-overexpression of β4 integrin and FAK positively correlated with advanced stages of human colon cancer tissues.

4.2.1 Co-Overexpression of β4 Integrin and FAX in Advanced Stage Human Colon Cancer Tissues To elucidate the relationship between β4 integrin and FAK in human colon cancer, we first explored the pathological relevance of β4 integrin and FAK in paired primary colon cancer tissues and normal mucosa counterparts by immunohistochemical staining. This analysis suggested that the co-expression of both β4 integrin and FAK is clinically relevant. To further attempt to investigate the clinicopathologic relevance of β4 integrin and FAK co-expression in human colon cancer, we analyzed the expression of β4 integrin and FAK in a cohort of 67 human colon cancer specimens with early (stage I) and advanced (stage II, III and IV) stage tumors. Our results indicated that β4 integrin and FAK were highly expressed in 63% and 82% of advanced stage tumors, respectively; whereas 80% and 60% of early stage tumors expressed low levels of β4 integrin and FAK, respectively (FIG. 8A, FIG. 8B). Alternatively, our data demonstrated that approximately 47.7% (32 out of 67) of colon cancer patients bear tumors with high expression of both β4 integrin and FAK. (FIG. 8C). Conversely, approximately 17.9% (12 out of 67) of patients displayed low levels of both proteins. Indeed, given a Spearman's γ correlation of 0.2860 (p=0.0189) (FIG. 8C), the statistical analyses reinforced a positive correlation between the expression level of β4 integrin and FAK in colon cancers. These results indicated that co-overexpression of β4 integrin and FAK positively correlates with development of advanced stage human colon cancer.

4.2.2 β4 Integrin Physically Interacts with a 25-Amino Acid Motif within the Amino-Terminal FAK in HCT-116 Human Colon Cancer Cells To investigate molecular mechanisms of β4 integrin-FAK signaling underlying human colon cancer progression, we performed biochemical analyses. First, we found that β4 integrin co-immunoprecipitated with FAK from primary colon cancer tissues but not from paired samples of normal mucosa (FIG. 9(A)). As expected, the interaction between β4 integrin and FAK was also detectable in human HCT-116 colon cancer cells, but not in human HeLa cervical cancer cells or non-tumorigenic HEK-293 human cells (FIG. 9(B)).

We then examined if β4 integrin could physically interact with FAK in human colon cancer using in vitro pull-down, assays and mutational analyses. We found that β4 integrin immunoprecipitated with recombinant GST-FAK/N400 (the first 400 amino acids of FAK) but not GST-FAK/N375 (the first 375 amino acids of FAK) in HCT-116 cell lysates (FIG. 9(C)), indicating that the 25-amino-acid motif (FAK/25aa, from the 376th to the 400th) within the amino-terminus of FAK is essential for physical interactions with β4 integrin.

We also assessed these 25 amino acids within FAK that are essential for β4 integrin binding by site-directed mutagenesis. Our results showed that mutations of three amino acids (Glu380, Lys381, and Gln382) within this region of FAK diminished its β4 integrin binding ability. A triple mutation mutant, FAK$^{E380A/K381A/Q382A}$, almost abolished FAK interaction with β4 integrin in HCT-116 cells, whereas β4 integrin binding remained intact with other FAK mutations of this 25-amino-acid motif, such as FAK$^{R385A/S386A}$ (FIG. 9D). Moreover, we further investigated that the FAK/25aa motif but not the FAK/25aa$^{E380A/K381A/Q382A}$ motif ablated the interaction between β4 integrin and FAK in HCT-116 cells (FIG. 9(E)). On the other hand, we have demonstrated that the intracellular juxtamembrane region (cytodomain) of β4 integrin is essential for interactions with FAK, and other regions, such as the type III FN-like repeats or the connecting segment between type III FN-like repeats are not involved. We next utilized mutational analyses to dissect the cytodomain of β4 integrin into the Na$^+$/Ca$^{2+}$ exchanger homologous motif (CalX) and CalX truncated region to further reveal which motif is responsible for interaction with FAK. Surprisingly, the intact cytodomain of β4 integrin was indispensable for interactions with FAK (FIG. 9F).

Figures 9A, 9B, 9C:
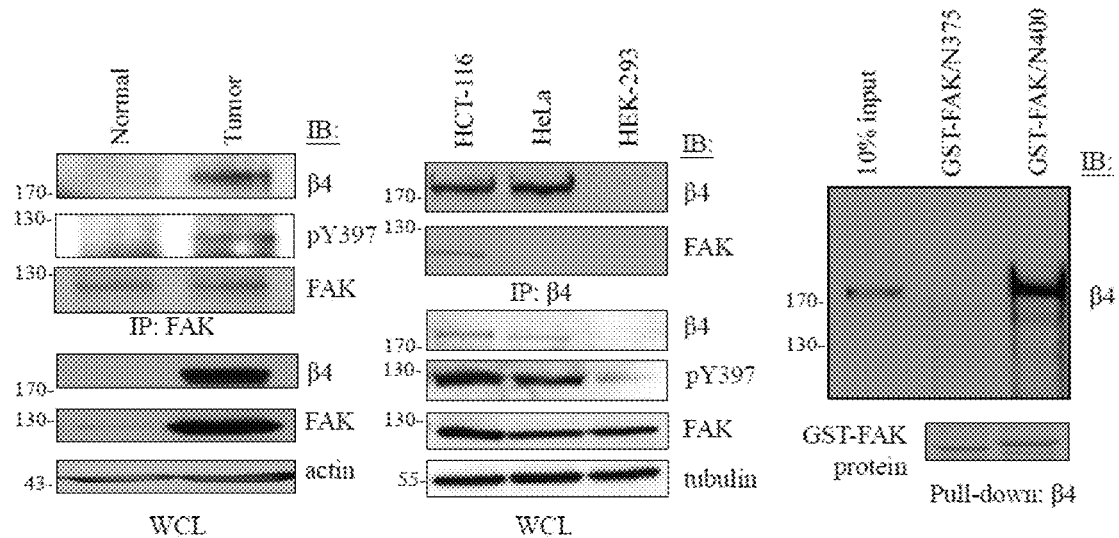
FIGS. 9(A)-9(F) show that the level of FAK autophosphorylation at Tyr397 was influenced by β4 integrin in human colon cancer.
Figures 9D, 9E, 9F:
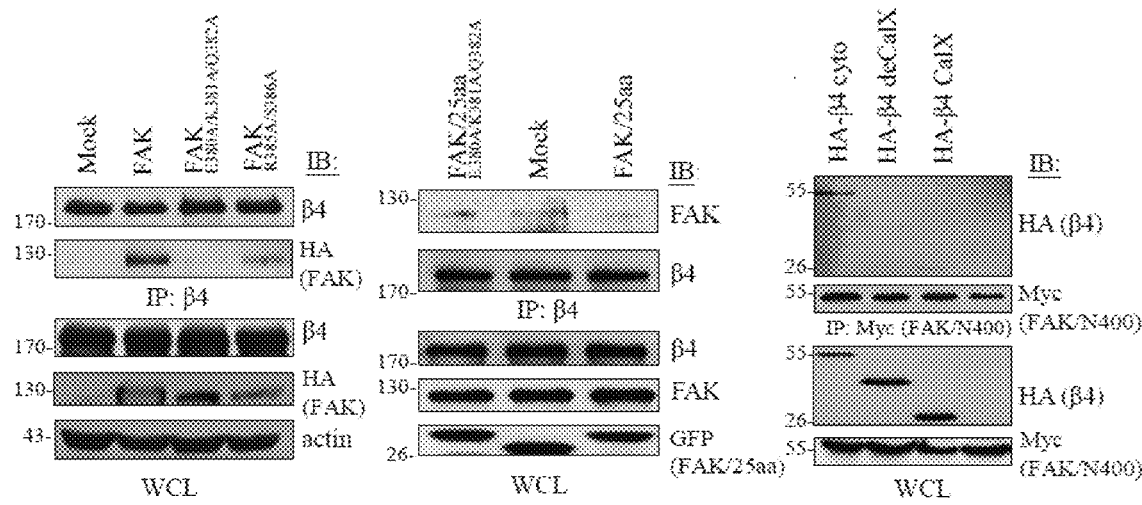
Figure 10A:
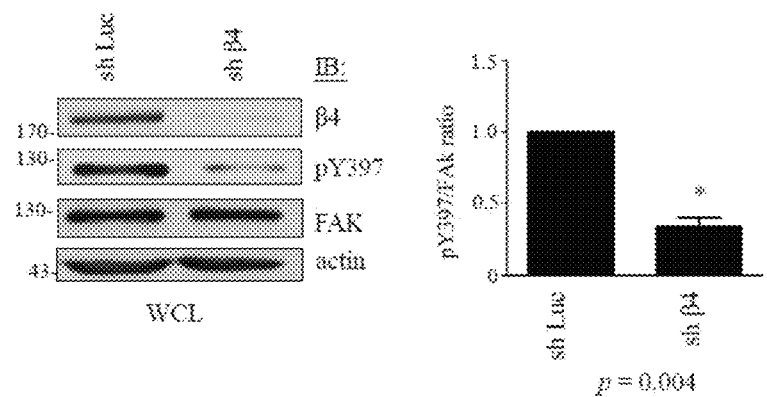
FIGS. 10(A)-10(C) show the interaction with β4 integrin promotes FAK autophosphorylation at Tyr397.
Figures 10B, 10C:
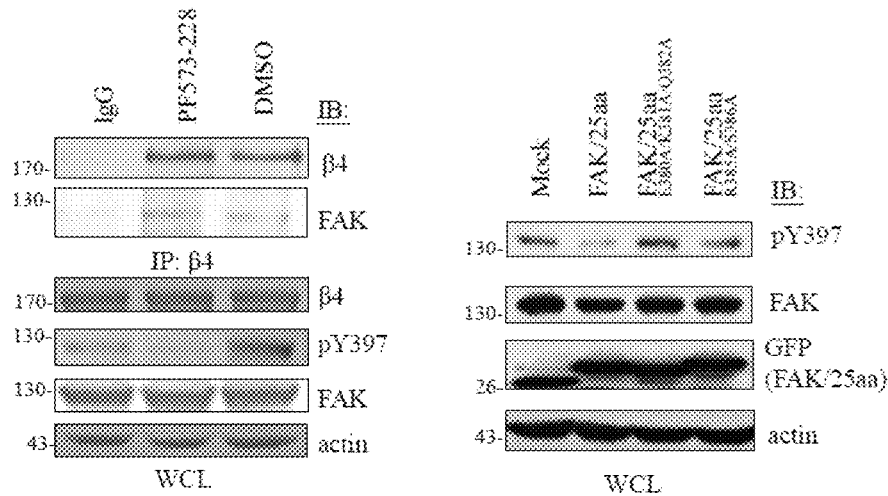

4.2.3 Interaction with β4 Integrin Leads to FAX Autophosphorylation in Human Colon Cancer Given that β4 integrin-bound FAX was highly phosphorylated at Tyr397 in human colon cancer (FIG. 9(B)), we found that β4 integrin regulated the phosphorylation of FAK at Tyr397, as β4 integrin-knockdown reduced the phosphorylation of FAK in HCT-116 human colon cancer cells (FIG. 10(A)). Moreover, the β4 integrin/FAK complex still formed when FAK activity was pharmacologically inhibited with PF-573,228 (FIG. 10(B)). These results indicate that the β4 integrin/FAK complex formation promotes Tyr397-autophosphorylation of FAK in human colon cancer.

The 25-amino-acid motif of FAK that is responsible for interacting with β4 integrin, contains the Tyr397-autophosphorylation site. We were therefore prompted to test whether the interaction between β4 integrin and FAK directly modulates the outcome of Tyr397-autophosphorylation of FAK. While overexpressing the FAK/25aa motif (resulting in competition and disruption of β4 integrin/FAK complex formation) as well as the triple mutant (FAK/25aa$^{E380A/K381A/Q382A}$, results in loss of interaction with β4 integrin) and double mutant (FAK/25aa$^{R385A/S386A}$, maintains interaction with β4 integrin), we found that the Tyr397-autophosphorylation of FAK was diminished in FAK/25aa- and FAK/25aa$^{R385A/S386A}$-transfected cells but remained in FAK/25aa$^{E380A/K381A/Q382A}$-transfectants, indicating that FAK-Tyr397 undergoes autophosphorylation when bound to β4 integrin (FIG. 10(C)). These results indicated that the interaction with β4 integrin enables FAK autophosphorylation at Tyr397 in human colon cancer.

Figures 11A, 11B, 11C:
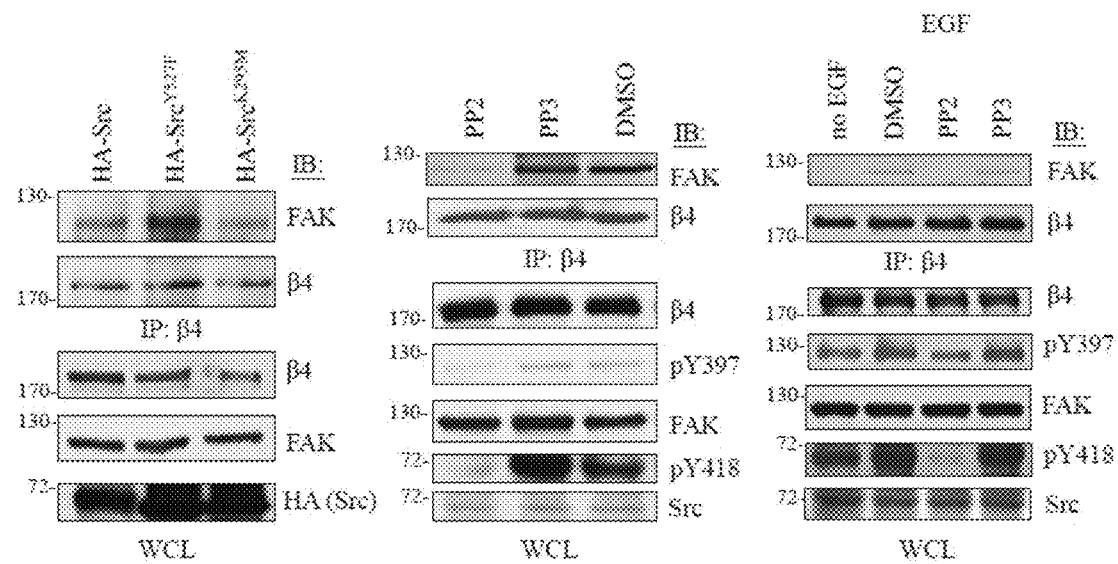
FIGS. 11(A)-11(C) show that AKT was the downstream effector of β4 integrin/FAK complexes. HCT-116 cells were transfected with GFP-FAK/25aa or its triple (FAK/25aa$^{E380A/K381A/Q382A}$) or double (FA K/25aa$^{R385A/S386A}$) mutant to reveal potential downstream signaling, including phospho-Ser473-AKT, phospho-Tyr118-paxillin, phospho-Thr180/Tyr182-p38 MAPK, phospho-Thr183/Tyr185-INK MAPK, and phospho-Thr202/Tyr204-ERK MAPK by Western blotting.

4.2.4 Activation of FAK Through Interaction With β4 Integrin is an EGFR/Src Dependent Manner The activity of Src family kinases (SFKs) is required for β4 integrin- and FAK-mediated signalings. To explore whether Src activity is essential for the β4 integrin/FAK complex formation as well as FAK activation in human colon cancer, we firstly investigated that the β4 integrin/FAK complex formation is increased in HCT-116 cells which were transfected with a constitutively active Src expression construct (Y527F) (FIG. 11(A)). Consistently, pharmacological blockade of Src activity by PP2 appeared to decrease the β4 integrin/FAK complex formation and to alleviate the FAK activation (FIG. 11(B)). Since EGF/EGFR signaling is essential for β4 integrin-mediated cancer functions through SFKs activity, both the β4 integrin and FAK association and FAK activation can be elevated in response to EGF stimulation but is ablated in the presence of PP2 (FIG. 11(C)). We suggested that the increase in FAK autophosphorylation at Tyr397 by interaction with β4 integrin in human colon cancer was due to the EGFR/Src signaling.

4.2.4 AKT as a Downstream Effector of β4 Integrin/FAK Complexes

Figure 12:
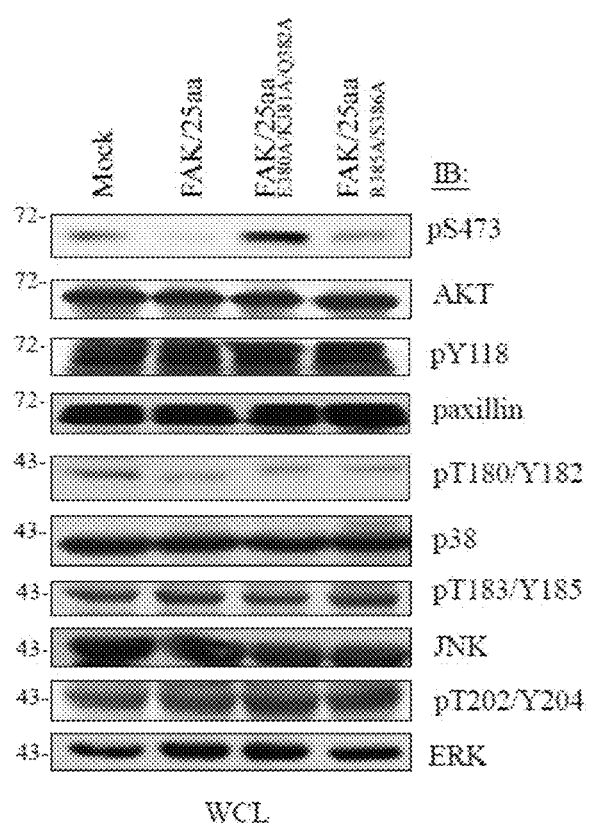
FIG. 12 shows that β4 integrin/FAK complex-mediated FAK activation were essential for colon cancer progression, anchorage-independent growth was impaired when FAK Tyr397-autophosphorylation was blocked with a pharmacological FAK inhibitor in HCT-116 cells.

We sought to determine the signaling events that emanate from β4 integrin/FAK complexes in HCT-116 cells. By testing several potential downstream signaling transducers, AKT was revealed to participate in β4 integrin/FAK complex-mediated signaling (FIG. 12). Consistently, FAK activity was also required for AKT phosphorylation (FIG. 14(A)). These results suggested that AKT is a potential downstream effector in β4 integrin/FAK complex-mediated signaling.

Figure 13A:
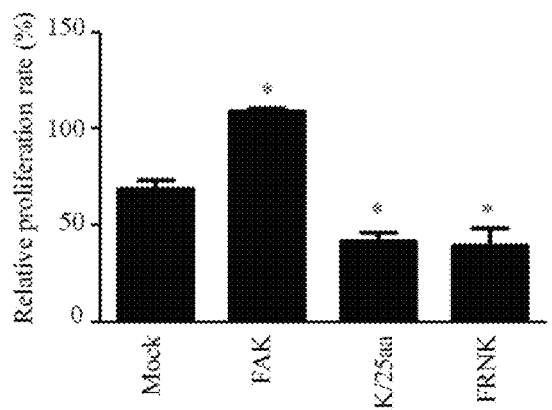
FIGS. 13(A)-13(C) shows that β4 integrin/FAK complexes regulate HCT-116 human colon cancer tumorigenesis.
Figure 13B:
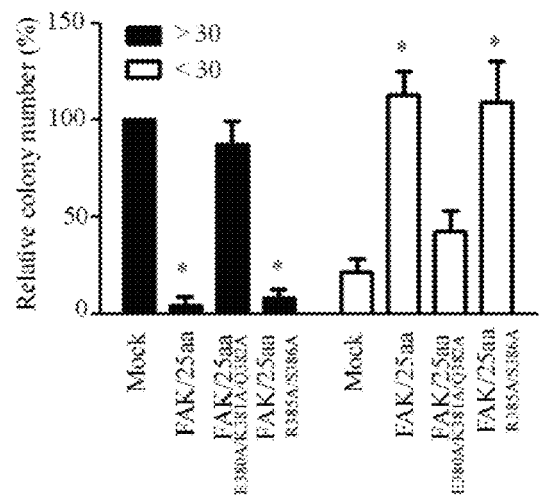
Figure 13C:
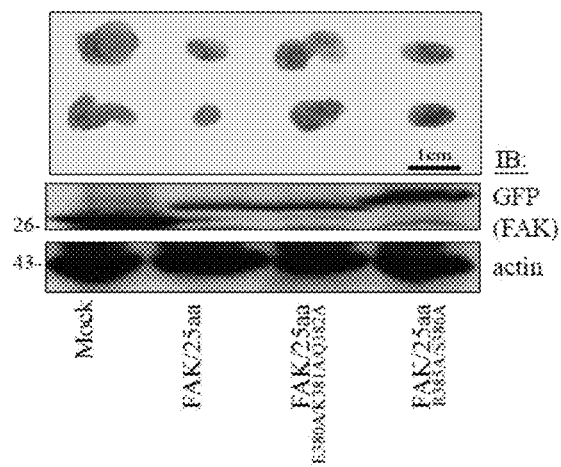
Figure 13C:
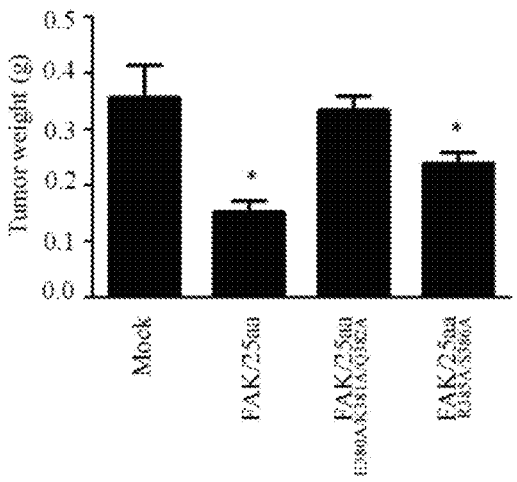

4.2.5 β4 Integrin/FAK Complexes are Essential for Human Colon Cancer Tumorigenesis In Vitro and In Vivo We then investigated functional effects of β4 integrin/FAK complexes in human colon cancer cells. To achieve this, we disrupted β4 integrin/FAK complexes by overexpressing FAK/25aa (FIG. 9(E)) and then subjected the cells to functional assays. Consistent with the role of FAX in cell proliferation, disruption of β4 integrin/FAK complexes impaired cell proliferation in HCT-116 cells (FIG. 13A). These results are analogous to blockade of FAK-mediated cell functions by over-expression of the dominant negative FAK, FRNK (FIG. 13(A)). Moreover, anchorage-independent growth was considerably decreased in the FAK/25aa and the FAK/25aa$^{R385A/S386A}$ transfectants compared with that in the mock and the FAK/25aa$^{E380A/K381A/Q382A}$-transfected cells (FIG. 13(B)). To further verify the above observations, an in vivo tumorigenesis assay was conducted using a xenograft mouse model subcutaneously implanted with HCT-116 cells. We found that the ectopic-expression of the FAK/25aa or the FAK/25aa$^{R385A/S386A}$, but not the FAK/25aa$^{E380A/K381A/Q382A}$, significantly reduced the volume and weight of implanted colon cancer tumors (FIG. 13(C)). Moreover, the protein expressions of the FAK/25aa and the mutants within the tumors were validated in the xenograft tumors (FIG. 13(C)). Together, our studies provide evidence for the role of β4 integrin/FAK complexes in colon cancer tumorigenesis.

4.2.6 Targeting the FAK Activity in Human Colon Cancer

Figure 14A:
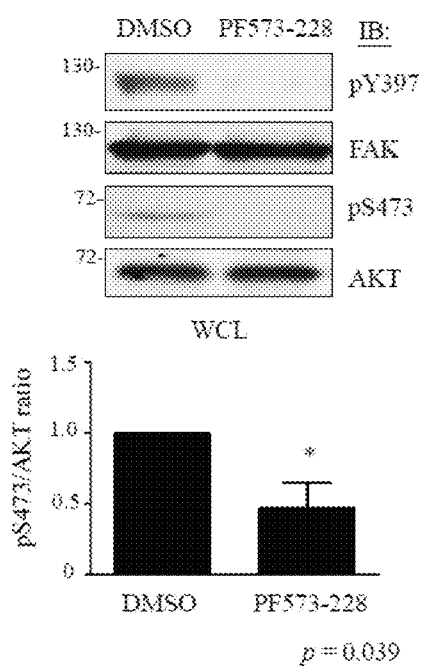
FIGS. 14(A)-14(B) show that blocking FAK activity impairs tumorigenesis of HCT-116 human colon cancer cells.
Figure 14B:
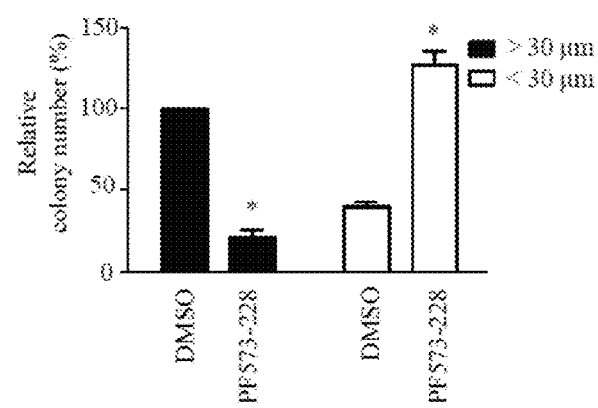

In agreement with β4 integrin/FAK complex-mediated FAK activation being essential for colon cancer progression, anchorage-independent growth was impaired when FAK Tyr397-autophosphorylation was blocked with a pharmacological FAK inhibitor in HCT-116 cells (FIG. 14(A) and FIG. 14(B)). Moreover, the anchorage-independent growth was ablated in FAK activation-reduced HCT-116 cells through the overexpression of the inactive FAK Y397F mutant (unpublished data). Our results provide a rationale for targeting FAK activity as a novel colon cancer intervention.

In conclusion, it was demonstrated in the present invention that β4 integrin and FAK physically and functionally interact with each other in vitro and in vivo. This interaction is modulated by EGF/Src signaling, which triggers a tyrosine phosphorylation cascade that regulates tumor proliferation, migration, and invasion as well as metastasis in vitro and in vivo. Several signaling mediators, i.e., AKT and p38MAPK, may play pivotal roles in β4 integrin/FAK-mediated tumor functions. The present invention demonstrates a crucial signaling module involved in the regulation of malignancy in triple-negative breast cancer and a novel target for future interventions and anti-cancer therapeutics.

REFERENCES

[1] Tejpar, S., et al., *Integrating biomarkers in colorectal cancer trials in the West and China*. Nat Rev Clin Oncol. 2015.

[2] Arvelo, F., F. Sojo, and C. Cotte, *Biology of colorectal cancer*. E cancer medical science, 2015.9: p. 520.

[3] Siegel, R., C. Desantis, and A. Jemal, *Colorectal cancer statistics*. 2014. CA Cancer J Clin, 2014. 64(2): p. 104-17.

[4] Sineshaw, H. M., A. S. Robbins, and A. Jemal, *Disparities in survival improvement for metastatic colorectal cancer by race/ethnicity and age in the United States*. Cancer Causes Control, 2014. 25(4): p. 419-23.

[5] Tai, Y. L., L. C. Chen, and T. L. Shen, *Emerging roles of focal adhesion kinase in cancer* Biomed Res Int, 2015. 2015: p. 690690.

[6] Golubovskaya, V. M., F. A. Kweh, and W. G. Cance, *Focal adhesion kinase and cancer*. Histol Histopathol, 2009. 24(4): p. 503-10.

[7] Lai, I. R., et al., *Phosphorylation of focal adhesion kinase at Tyr397 in gastric carcinomas and its clinical significance*. Am J Pathol, 2010. 177(4): p. 1629-37.

[8] Cance, W. G., et al., *Immunohistochernical analyses of focal adhesion kinase expression in benign and malignant human breast and colon tissues: correlation with preinvasive and invasive phenotypes*. Clin Cancer Res, 2000. 6(6): p. 2417-23.

[9] Han, N. M., et al., *Overexpression of focal adhesion kinase (p125FAK) in human colorectal carcinoma liver metastases: independence from c-sic or c-yes activation*. Ann Surg Oncol, 1997. 4(3); p. 264-8.

[10] Yu, H. G., et al, *Rapid tyrosine phosphorylation of focal adhesion kinase, paxillin, and p130Cas by gastrin in human colon cancer cells*. Biochem Pharmacol, 2004, 67(1): p. 135-46.

[11] H. G., et al., *Enhanced expression of cholecystokinin-2 receptor promotes the progression of colon cancer through activation of focal adhesion kinase*. Int J Cancer, 2006. 119(12): p. 2724-32.

[12] Heftier, M., et al., *Focal adhesion kinase autophosphorylation inhibition decreases colon cancer cell growth and enhances the efficacy of chemotherapy*, Cancer Biol Ther, 2013. 14(8): p. 761-72.

[13] Thakur, R., et al., *Inhibition of STAT3, FAK and Src mediated signaling reduces cancer stem cell load, tumorigenic potential and metastasis in breast cancer* Sci Rep, 2015. 5: p. 10194.

[14] Mitra, S. K. and D. D. Schlaepfer, *Integrin-regulated FAK-Src signaling in normal and cancer cells*. Curr Opin Cell Riot, 2006. 18(5): p. 516-23.

[15] Chu, P. Y., et al., *Tyrosine phosphorylation of growth factor receptor-bound protein-7 by focal adhesion kinase in the regulation of cell migration, proliferation, and tumorigenesis*. J Biol Chem, 2009. 284(30): p. 20215-26.

[16] Thamilselvan, V., D. H. Craig, and M. D. Basson, *FAK association with multiple signal proteins mediates pressure-induced colon cancer cell adhesion via a Src-dependent PI3K/Akt pathway*. FASEB J, 2007. 21(8): p. 1730-41.

[17] McLean, G. W., et al., *The role of focal-adhesion kinase in cancer—a new therapeutic opportunity*. Nat Rev Cancer, 2005. 5(7): p. 505-15.

[18] Borradori, L. and A. Sonnenberg, *Structure and function of hemidesmosomes: more than simple adhesion complexes*. J Invest Dermatol, 1999. 112(4): p. 411-8.

[19] Boelens, M. C., et al., *Differential expression and distribution of epithelial adhesion molecules in non-small cell lung cancer and normal bronchus*. J Clin Pathol, 2007. 60(6): p. 608-14.

[20] Ni, H., et al., *Upregulation of a functional form of the beta4 integrin subunit in colorectal cancers correlates with c-Myc expression*. Oncogene, 2005. 24(45): p. 6820-9.

[21] Chung, J., et *Integrin (alpha 6 beta 4) regulation of eIF-4E activity and VEGE translation: a survival mechanism for carcinoma cells*. J Cell Biol, 2002. 158(1): p. 165-74.

[22] Gianeotti, F. G., *Targeting integrin beta4 for cancer and anti-angiogenic therapy*. Trends Pharmacol Sci. 2007. 28(10): p. 506-11.

[23] Bertotti, A., P. M. Comoglio, and L. Trusolino, *Beta4 integrin activates a Shp2-Src signaling pathway that sustains HGF-induced anchorage-independent growth*. J Cell Biol, 2006. 175(6): p. 993-1003.

[24] Guo, W., et al., *Beta 4 integrin amplifies ErbB2 signaling to promote mammary tumorigenesis*. Cell, 2006. 126(3): p. 489-502.

[25] Bertotti, A., P. M. Comoglio, and L. Trusolino, *Beta4 integrin is a transforming molecule that unleashes Met tyrosine kinase tumorigenesis*. Cancer Res, 2005. 65(23): p. 10674-9.

[26] Shaw, L. M., et al., *Activation of phosphoinositide 3-OH kinase by the alpha6beta4 integrin promotes carcinoma invasion*. Cell. 1997. 91(7): p. 949-60.

[27] Murata, T., et al., *Localization of FAK is related with colorectal carcinogenesis*. Int J Oncol, 2008. 32(4): p. 791-6.

[28] Beaulieu, J. F., *Integrin alpha6beta4 in colorectal cancer*. World J Gastrointest Pathophysiol, 2010. 1(1): p. 3-11.

[29] Tai, Y. L., et al., *An EGFR/Src-dependent β4 integrin/FAK complex contributes to malignancy of breast cancer*. scientific reports, 2015. in press.

[30] Abdel-Ghany, M., et al., *Focal adhesion kinase activated by beta(4) integrin ligation to mCLCA1 mediates early metastatic growth*. J Biol Chem, 2002. 277(37): p. 34391-400.

[31] Chen, Q., et al., *Down-regulation of Gli transcription factor leads to the inhibition of migration and invasion of ovarian cancer cells via integrin beta4-mediated FAK signaling*. PLoS One, 2014. 9(2): p. e88386.

[32] Shen, T. L., D. C. Han, and J. L. Guan, *Association of Grb7 with phosphoinositides and its role in the regulation of cell migration*. J Biol Chem, 2002. 277(32): p. 29069-77.

[33] Chu, P. Y., et al., *EGF-induced Grb7 recruits and promotes Ras activity essential for the tumorigenicity of Sk-Br3 breast cancer cells*. J Biol Chem, 2010. 285(38): p. 29279-85.

[34] Zhang, S. and D. Yu, *Targeting Src family kinases in anti-cancer therapies: turning promise into triumph*. Trends Pharmacol Sci, 2012. 33(3): p. 122-8.

[35] Mariotti, A., et al., *EGF-R signaling through Fyn kinase disrupts the function of integrin alpha6beta4 at hemidesmosomes: role in epithelial cell migration and carcinoma invasion*. J Cell Biol, 2001. 155(3): p. 447-58.

[36] Zhao, J. and J. L. Guan, *Signal transduction by focal adhesion kinase in cancer*. Cancer Metastasis Rev, 2009. 28(1-2): p. 35-49.

[37] Parsons, J. T., et al., *Focal adhesion kinase: targeting adhesion signaling pathways for therapeutic intervention.* Clin Cancer Res, 2008. 14(3): p. 627-32

[38] Weiner, T. M., et al., *Expression of focal adhesion kinase gene and invasive cancer*. Lancet, 1993. 342 (8878): p, 1024-5.

[39] Owens, L. V., et al., *Overexpression of the focal adhesion kinase (p125FAK) in invasive human tumors*. Cancer Res, 1995. 55(13): p. 2752-5.

[40] Lark, A. L., et al., *Overexpression offbeat adhesion kinase in primary colorectal carcinomas and colorectal liver metastases: immunohistochemistry and real-time PCR analyses*. Clin Cancer Res, 2003. 9(1): p. 215-22.

[41] Roberts, W. G, et al., *Antitumor activity and pharmacology of a selective focal adhesion kinase inhibitor, PF-562,271*. Cancer Res, 2008.58(6): p. 1935-44.

[42] Sun, H., et al., *Bioluminescent imaging study: FAK inhibitor PF-562,271, preclinical study in PC3M-luc-C6 local implant and metastasis xenograft models*. Cancer Biol Ther, 2010. 10(1): p. 38-43.

[43] Lietha, D., et al., *Structural basis for the autoinhibition of focal adhesion kinase*. Cell, 2007. 129(6): p. 1177-87.

[44] Cooper, L A., T. L. Shen, and J. L. Guan, *Regulation of focal adhesion kinase by its amino-terminal domain through an autoinhibitory interaction*. Mol Cell Biol, 2003.23(22): p. 8030-41,

[45] Dunty, J. M., et al., *FERM domain interaction promotes FAK signaling*. Mol Cell Biol, 2004. 24(12): p. 5353-68.

We claim:

1. A method for treatment or prevention of colon cancer, comprising administering to a subject in need thereof a molecule effective to block the binding of β4 integrin and focal adhesion kinase (FAK), wherein the molecule is FAK/11aa consisting of the amino acid sequence SEQ ID NO: 2, or FAK/25aa consisting of the amino acid sequence SEQ ID NO: 3.

2. The method of claim 1, wherein the molecule is FAK/11aa consisting of the amino acid sequence of SEQ ID NO: 2.

3. The method of claim 1, wherein the molecule is FAK/25aa consisting of the amino acid sequence of SEQ ID NO: 3.

* * * * *